US010028941B2

(12) United States Patent
Vranderick et al.

(10) Patent No.: US 10,028,941 B2
(45) Date of Patent: *Jul. 24, 2018

(54) COMPOSITION FOR THE MANAGEMENT OF NAUSEA AND VOMITING

(71) Applicant: DUCHESNAY INC., Québec (CA)

(72) Inventors: Manon Vranderick, Québec (CA); Jean-Luc St-Onge, Québec (CA); Michele Gallo, Québec (CA); Éric Gervais, Québec (CA)

(73) Assignee: DUCHESNAY INC., Blainville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/907,248

(22) PCT Filed: Mar. 13, 2014

(86) PCT No.: PCT/CA2014/050231
§ 371 (c)(1),
(2) Date: Jan. 22, 2016

(87) PCT Pub. No.: WO2015/010194
PCT Pub. Date: Jan. 29, 2015

(65) Prior Publication Data
US 2016/0143892 A1 May 26, 2016

Related U.S. Application Data
(60) Provisional application No. 61/856,971, filed on Jul. 22, 2013.

(51) Int. Cl.
A61K 31/4402 (2006.01)
A61K 31/4415 (2006.01)
A61K 31/525 (2006.01)
A61K 31/7076 (2006.01)
A61K 9/00 (2006.01)
A61K 31/519 (2006.01)
A61K 31/675 (2006.01)
A61K 31/661 (2006.01)
A61K 31/7084 (2006.01)

(52) U.S. Cl.
CPC ........ A61K 31/4402 (2013.01); A61K 9/0053 (2013.01); A61K 31/4415 (2013.01); A61K 31/519 (2013.01); A61K 31/525 (2013.01); A61K 31/661 (2013.01); A61K 31/675 (2013.01); A61K 31/7076 (2013.01); A61K 31/7084 (2013.01)

(58) Field of Classification Search
CPC ............ A61K 31/4402; A61K 31/7076; A61K 31/519; A61K 31/675; A61K 31/4415; A61K 31/525; A61K 9/0053; A61K 31/661; A61K 31/7084; A61K 2300/00
USPC .................................................. 514/47, 251
See application file for complete search history.

(56) References Cited

U.S. PATENT DOCUMENTS

| 4,842,867 A | 6/1989 | Ayer et al. |
| 6,197,329 B1 | 3/2001 | Hermelin et al. |
| 6,340,695 B1 | 1/2002 | Gervais |
| 6,924,273 B2 | 8/2005 | Pierce |
| 7,704,542 B2 | 4/2010 | Bydlon et al. |
| 9,089,489 B2 | 7/2015 | Vranderick et al. |
| 9,439,920 B2 * | 9/2016 | Vranderick ........ A61K 31/7076 |
| 9,452,181 B2 | 9/2016 | Vranderick et al. |
| 2007/0141147 A1 | 6/2007 | Heil et al. |
| 2009/0004281 A1 | 1/2009 | Nghiem et al. |
| 2012/0093923 A1 | 4/2012 | Miller et al. |
| 2014/0314680 A1 | 10/2014 | Vranderick et al. |
| 2015/0025032 A1 | 1/2015 | Vranderick et al. |
| 2015/0025033 A1 | 1/2015 | Vranderick et al. |

FOREIGN PATENT DOCUMENTS

| CA | 2 316 277 | 7/1999 |
| CA | 2 350 195 A1 | 8/2001 |
| JP | 2002-543106 | 12/2002 |
| JP | 2004-521146 | 7/2004 |
| JP | 2008-543723 | 12/2008 |
| WO | WO 99/33448 | 7/1999 |
| WO | WO 03/00263 A1 | 1/2003 |
| WO | WO 2006/017341 A2 | 2/2006 |

(Continued)

OTHER PUBLICATIONS

Magee et al. Diagnosis and Management of Nausea and Vomiting in Pregnancy. Fetal and Maternal Medicine Review 2006; 17:1 45-67. doi:10.1017/S0965539505001701.*
Atanackovic et al. The Safety of Higher Than Standard Dose of Doxylamine-Pyridoxine (Diclectin®) for Nausea and Vomiting of Pregnancy. J Clin Pharmacol 2001;41:842-845.*
Sinigaglia-Coimbra et al. Riboflavin Deficiency, Brain Function, and Health. V.R. Preedy et al. (eds.), Handbook of Behavior, Food and Nutrition, p. 2427-2449, 2011. DOI 10.1007/978-0-387-92271-3_153, © Springer Science+Business Media, LLC 2011.*
Abbas et al., "Genetic Control of Biosynthesis and Transport of Riboflavin and Flavin Nucleotides and Construction of Robust Biotechnological Producers," *Microbiol. Mol. Biol. Rev.*, 75 (2):321-360 (2011).

(Continued)

Primary Examiner — Yin-Horng Shiao
(74) Attorney, Agent, or Firm — Finnegan Henderson, Farabow, Garrett & Dunner LLP

(57) ABSTRACT

A pharmaceutical dosage system comprising (a) an effective amount of one or more of Doxylamine, an analog thereof, a derivative thereof, a prodrug thereof, a metabolite thereof and/or a salt thereof; (b) an effective amount of one or more of (i) Pyridoxine, (ii) an analog thereof, (iii) a derivative thereof, (iv) a prodrug thereof, (v) a metabolite thereof and (vi) a salt of any of (i)-(v); and (c) an effective amount of one or more compounds of formula (I) wherein R is H, $PO_3$ or. The system exhibits an improved pharmacokinetic profile relative to the current Diclectin®/Diclegis® formulation and is useful for example for the alleviation of the symptoms of nausea and vomiting, for example in the case of nausea and vomiting of pregnancy (NVP).

19 Claims, 5 Drawing Sheets

(56) References Cited

FOREIGN PATENT DOCUMENTS

| WO | WO 2006/087116 | 8/2006 |
| WO | WO 00/066082 | 11/2006 |
| WO | WO 2009/092601 | 7/2009 |
| WO | WO 2011/111818 | 9/2011 |
| WO | WO 2011/124953 | 10/2011 |
| WO | WO 2011/163206 | 12/2011 |
| WO | WO 2012/112437 A1 | 8/2012 |
| WO | WO 2012/170676 A1 | 12/2012 |
| WO | WO 2013/123569 A1 | 8/2013 |

OTHER PUBLICATIONS

Adelekan et al., "Dependence of pyridoxine metaboiism on riboflavin status in sickle cell patients," *Am J. Clin. Nutr.*, 46: 86-90 (1987).

Al-Awadi et al., "Complexes of vitamin $B_6$. XIV* Kinetics and reaction mechanism of the interaction of pyridoxal-5'-phosphate with Cu(II)-pyridoxamine complexes," *Inorganica Chimica Acta*, 67:131-138 (1982).

Aw et al., "Uptake of Riboflavin by Isolated Rat Liver Cells," *J. Nutr.*, 113(6): 1249-1254 (1983).

Barile et ., "Flavin adenine dinucleotide and flavin mononucleotide metabolism in rat liver The occurrence of FAD pyrophosphatase and FMN phosphohydrolase in isolated mitochondria," *Eur. J. Biochem.*,249(3): 777-785 (1997).

Bohney et al., "Identification of $Lys^{190}$ as the primary binding site for pyridoxal 5'-phosphate in human serum albumin," *FEBS Lett.*, 298(2-3): 266-268 (1992).

Capo-Chichi et al., "Analysis of riboflavin and riboflavin cofactor levels in plasma by high-performance, liquid chromatography," *Journal of Chromatography B*, 739: 219-224 (2000).

Casirola et al., "Riboflavin uptake by rat small intestinal brush border membrane vesicles: A dual mechanism involving specific membrane binding," *J. Membrane Biol.*, 135: 217-223 (1993).

Di Salvo et al., "Vitamin $B_6$ salvage enzymes: Mechanism, structure and regulation," *Biochimica et Biophysica Acta*, 1814: 1597-1608 (2011).

Fazekas et al, "Studies on the Biosynthesis of Flavin Nucleotides from $2-^{14}C$-Riboflavin by Rat Liver and Kidney," 9 *Can. J. Biochem.*, 51(6): 772-782 (1973).

Gastaldi et al., "Riboflavin Phosphorylation Is the Crucial Event in Riboflavin Transport by Isolated Rat Enterocytes," *J Nutr.*, 130(10): 2556-2561 (2000).

Gill, "Investigating Sources of Variability in Pharmacological Response to Nausea and Vomiting of Pregnancy," A thesis submitted in conformity with the requirements for the degree of Doctor of Philosophy. Graduate Department of Pharmacology and Toxicology Faculty of Medicine University of Toronto (2010).

Hamfelt, "Pyridoxal phosphate concentration and aminotransferase activity in human blood cells," *Clinica Chimica Acta*, 16(1): 19-28 (1967).

Hayashi et al., "Recent Topics in Pyridoxal 5'-Phosphate Enzyme Studies," *Annu. Rev. Biochem.*, 59: 87-110 (1990).

Hustad et al., "Quantification of Riboflavin, Flavin Mononucleotide, and Flavin Adenine Dinucleotide in Human Plasma by Capillary Eiectrophoresis and Laser-induced Fluorescence Detection," *Clinical Chemistry*, 45(6): 862-868 (1999).

Hustad et al., "Riboflavin, Flavin Mononucleotide, and Ravin Adenine Dinucleotide in Human Plasma and Erythrocytes at Baseline and after Low-Dose Riboflavin Supplementation," *Clinical Chemistry*, 48(9): 1571-1577 (2002).

Jusko et al., "Absorption, Metabolism, and Excretion of Riboliavin-5'-phosphate in Man," *J. Pharm. Sci.*, 56(1): 58-62 (1967).

Kim et al., Interactions of Pyridoxal Kinase and Aspartate Aminotransferase Emission Anisotropy and Compartmentation Studies, *J. Biol. Chem.*, 263(27): 13712-13717 (1988).

Lakshmi et al., "Tissue pyridoxal phosphate concentration and pyridoxaminephosphate oxidase activity in riboflavin deficiency in rats and man," *Br. J. Nutr.*, 32:249-455 (1974).

Lakshmi et al., "Regulation of Blood Pyridoxal Phosphate in Riboflavin Deficiency in Man," *Nutr. Metabol.*, 20: 228-233 (1976).

Lakshmi et al., "Metabolism of $[2-^{14}C]$pyridoxine in riboflavin deficiency," *Biochemical Medicine*, 22(3): 274-281 (1979).

Leibman et al., "Vitamin 8-6 metabolic enzymes in blood and placenta of pregnant mice," *J. Nutr.*, 120(2):178-184 (1990).

Löwik et al., "Interrelationships between riboflavin and vitamin B6 among elderly people (Dutch Nutrition Surveillance System)," *Int. J. Vitam. Nutr. Res.*, 64(3):198-203 (1994).

Madigan et al, "Riboflavin and vitamin B-6 intakes and status and biochemical response to riboflavin supplementation in free-living elderly people," *Am. J. Clin. Nutr.*, 68: 389-395 (1998).

Mandula et al., "Synthesis of Riboflavin Nucleotides by Mature Human Erythrocytes," *Blood*, 36: 491-499 (1970).

McCormick, "Two interconnected B vitamins: riboflavin and pyridoxine," *Physiol. Rev.*, 69(4):1170-1198 (1989).

Mushtaq et al, "Erythrocyte pyridoxamine phosphate oxidase activity: a potential biomarker of riboflavin status?" *Am. J. Clin. Nutr.*, 90(5): 1151-1159 (2009).

Muttart et al., "Enhanced riboflavin incorporation into flavins in newborn riboflavin-deficient rats," *Am J Physiol*, 233(5): E397-E401, (1977).

Rasmussen et al., "Pyridoxamine (pyridoxine) 5'-phosphate oxidase activity in rat tissues during development of riboflavin, or pyridoxine deficiency (40589)." *Proc. Soc. Exp. Biol. Med.*, 161: 527-530 (1979).

Rasmussen et al., "Effect of strain, sex, and dietary riboflavin on pyridoxamine (pyridoxine) 5'-phosphate oxidase activity in rat tissues." *J. Nutr.*, 110:1940-1946 (1980).

Ramsay et al., "Vitamin cofactor saturation indices for riboflavin, thiamin, and pyridoxine in placental tissue of Kenyan women," *Am. J. Clin. Nutr.*, 37:969-973 (1983).

Rivlin et al., "Regulation of flavoprotein enzymes in hypothyroidism and in riboflavin deficiency," *Adv. Enzyme Regul.*, 8: 239-250 (1970).

Sasinowski et al., "Quantum of effectiveness evidence in FDA's approval of orphan drugs (Cataloguing FDA's Flexibility in Regulating Therapies for Persons with Rare Disorders)," *National Organization for Rare Disorders*, 27 pages (2011).

Sauberlich, "Interactions of Thiamin, Riboflavin, and Other B-Vitamins," *Annals of the New York Academy of Sciences*, 355: 80-97 (1980).

Toney, "Reaction specificity in pyridoxal phosphate enzymes," *Archives of Biochemistry and Biophysics*, 433: 279-287 (2005).

Trumbo et al., "Vitamin B-6 status indices are lower in pregnant than in nonpregnant women but urinary excretion of 4-pyrdoxic acid does not differ," *J. Nutr.*, 123(12): 2137-2141 (1993).

Wan et al., "Increased plasma pyridoxal-5'-phosphate when alkaline phosphatase activity is reduced in moderately zinc-deficient rats," *Biol. Trace Elem. Res.*, 39: 203-210 (1993).

Yoshimine, "Transport and phospho-dephosphorylation of thiamin and riboflavin in rat everted intestinal sacs," *Mie Med. J.*, 34: 37-17 (1984).

Zempleni et al., "The utilization of intravenously infused pyridoxine in humans." *Clinica Chimica Acta*, 229: 27-36 (1994).

Zempleni, "Determination of Riboflavin and Flavocoenzymes in Human Blood Plasma by High-Performance Liquid Chromatography," *Ann. Nutr. Metab.*, 39: 224-226 (1995).

Zempleni et al., "Pharmacokinetics of orally and intravenously administered riboflavin in healthy humans," *Am. J. Clin. Nutr.*, 63: 54-66 (1996).

Examination Report for lsraeli Patent Application No. 233644 dated Mar. 2, 2015 (including machine translation) (6 pages).

Patent Examination Report No. 1 for Australian Patent Application No. 2013224598 dated Mar. 5, 2015 (3 pages).

Notice of Reasons for Rejection for Japanese Patent Application No. 2014-557951 dated Mar. 27, 2015 (6 pages).

Extended European Search Report for European Patent Application No. 13751706.6 dated Mar. 31, 2015 (7 pages).

(56) References Cited

OTHER PUBLICATIONS

Decision of Rejection for Japanese Application No. 2014-557951, dated Sep. 14, 2015, (4 pages).
Reply to Office Action under 37 C.F.R. § 1.111 filed Dec. 23, 2014, in U.S. Appl. No. 14/226,214 (19 pages).
Final Office Action dated Feb. 12, 2015, in U.S. Appl. No. 14/228,214, (22 pages).
Reply to Final Office Action under 37 C.F.R. § 1.116 filed Apr. 13, 2015, in U.S. Appl. No. 14/228,214. (15 pages).
Office Action dated Aug. 26, 2015, in U.S. Appl. No. 14/228,214, (22 pages).
Office Action dated Sep. 5, 2014, in U.S. Appl. No. 14/228,228, (8 pages).
Response to Restriction Requirement filed Nov. 4, 2014, in. U.S. Appl. No. 14/228,228 (2 pages).
Office Action dated Dec. 1, 2014, in U.S. Appl. No. 14/228,228, (10 pages).
Reply to Office Action under 37 C.F.R. § 1.111 filed Feb. 27, 2015, in U.S. Appl. No. 14/228,228 (16 pages).
Notice of Allowance dated Mar. 23, 2015, in U.S. Appl. No. 14/228,228, (9 pages).
Office Action dated Oct. 30, 2015, in U.S. Appl. No. 14/746,635, (11 pages).
Reply to Office Action filed Jan. 28, 2016, in U.S. Appl. No. 14/746,635 (2 pages).
Office Action dated Nov. 30, 2015, in U.S. Appl. No. 14/839,859, (6 pages).
Response to Restriction Requirement filed Jan. 28, 2016, in U.S. Appl. No. 14/839,859 (4 pages).
Ashkenazi-Hoffnung et al., "Evaluation of the Efficacy and Safety of Bi-Daily Combination Therapy with Pyridoxine and Doxylamine for Nausea and Vomiting of Pregnancy," *IMAJ*, 15(1): 23-26 (2013).
Gill et al., "Systemic Bioavailabillity and Pharmacokinetics of the Doxylamine—Pyridoxine Delayed-Release Combination (Diclectin)," *Ther Drug Monit*, 33(1):115-119 (2011).
Koren et al., "Effectiveness of delayed-release doxylamine and pyridoxine for nausea and vomiting of pregnancy: a randomized placebo controlled trial," *Am J Obstet & Gynecol.*, 203(6): 571.e1-7 (2010).
Nulman et al., "Pharmacokinetic comparison of a delayed-release combination of doxylamine succinate and pyridoxine hydrocholoride (Diclectin®) and oral solutions of these drugs in healthy women of childbearing age," *Can J Clin Pharmacol.*, 16(3): e400-e406 (2009).
Rowland, "Pharmacokinetics of doxylamine given as Bendectin® in the pregnant monkey and baboon," *Reprod Toxicol.*, 3:197-202 (1989).
Slikker Jr et al., "Pharmacokinetics of doxylamine, a component of Bendectin®, In the rhesus monkey," *Reprod Toxicol.*, 3: 187-196 (1989).
Preliminary Amendment filed Mar. 28, 2014, in co-pending U.S. Appl. No. 14/228,228 (8 pages).
Office Action dated Jun. 12, 2014, in U.S. Appl. No. 14/228,214.
Amendment and Response to Restriction Requirement filed Aug. 11, 2014, in U.S. Appl. No. 14/228,214.
Office Action dated Sep. 23, 2014, in U.S. Appl. No. 14/228,214.
Office Action dated Aug. 24, 2015, in U.S. Appl. No. 14/506,387, (20 pages).
Reply to Office Action and Summary of Examiner Interview filed Feb. 24, 2016, in U.S. Appl. No. 14/506,387 (14 pages).
Notification of Transmittal of the International Search Report and the Written Opinion of the International Searching Authority, or the Declaration, for PCT International Application No. PCT/CA2012/050103, dated Oct. 18, 2012.
Notification of Transmittal of the International Search Report and the Written Opinion of the International Searching Authority, or the Declaration, for PCT International Application No. PCT/CA2013/050125, dated Apr. 25, 2013.
Notification of Transmittal of the International Search Report and the Written Opinion of the International Searching Authority, or the Declaration, for PCT International Application No. PCT/CA2014/050231, dated Jun. 5, 2014, (14 pages).
Notification of Transmittal of the International Search Report and the Written Opinion of the International Searching Authority, or the Declaration, for PCT International Application No. PCT/CA2014/050828, dated Dec. 4, 2014, (11 pages).
Mexican Patent Application Publication No. MX 2011010004 A, filed in the Mexican Intellectual Patent Office on Sep. 23, 2011 (27 pgs.).
Coimbra et al., *High doses of riboflavin and the elimination of dietary red meat promote the recovery of some motor functions in Parkinson's disease patients*, Brazilian J. Med. Biol. Res. (2003) 36: 1409-1417 (9 pgs.).
Response to Office Action filed Feb. 26, 2016 in U.S. Appl. No. 14/228,214 (12 pages).
Substantive Examination Report Notice dated Oct. 23, 2017 in Saudi Arabia Patent Appl. No. 516370443 (11 pages).
Harker et al., *Treating nausea and vomiting during pregnancy: case progression*, 328 BMJ 337 (2004), and Internet comments (10 pages).
Notice of Reasons for Rejection in Japanese Patent Application No. 2016-528268 (Dec. 25, 2017) (6 pages (including translation)).
Korede et al., *Plasma Vitamin B-6 Concentrations of Healthy Teenagers Given Dietary Supplements of Water Soluble Vitamins and Iron*, 12 Nutr. Res.; 825-831 (1992) (7 pages).

\* cited by examiner

One-way ANOVA: PLP AUC 0-12h versus treatment

```
Source  DF      SS     MS     F      P
treatm   3   40745  13582  2.47  0.080
Error   32  176051   5502
Total   35  216796

S = 74.17   R-Sq = 18.79%   R-Sq(adj) = 11.18%
```

```
                              Individual 95% CIs For Mean Based on
                              Pooled StDev
Level   N    Mean   StDev  --+---------+---------+---------+-------
PA-DR  12  256.36   85.96                (--------*--------)
PLP     8  191.05   63.35  (---------*----------)
PYL     8  220.55   53.18       (----------*----------)
R5P     8  283.79   81.83                     (----------*---------)
                           --+---------+---------+---------+-------
                           150       200       250       300

Pooled StDev = 74.17
```

One-way ANOVA: PLP AUC 0-2h versus treatment

```
Source  DF      SS     MS     F      P
treat    3   845.2  281.7  4.56  0.010
Error   29  1791.3   61.8
Total   32  2636.4

S = 7.859   R-Sq = 32.06%   R-Sq(adj) = 25.03%

Individual 95% CIs For Mean Based on
                            Pooled StDev
Level   N    Mean   StDev   ---------+---------+---------+---------+
PA-IR   9  20.833   7.190    (-------*------)
PLP     8  20.475   7.030   (-------*-------)
PYL     8  24.650   7.556        (-------*-------)
R5P     8  33.125   9.502                    (-------*-------)
                            ---------+---------+---------+---------+
                                  21.0      28.0      35.0      42.0

Pooled StDev = 7.859
```

COMPOSITION FOR THE MANAGEMENT OF NAUSEA AND VOMITING

CROSS-REFERENCE TO RELATED APPLICATIONS

This application claims the benefit of U.S. provisional application Ser. No. 61/856,971, filed on Jul. 22, 2013, which is incorporated herein by reference in its entirety.

TECHNICAL FIELD

The present invention generally relates to pharmaceutical compositions and dosage systems, such as pharmaceutical compositions and dosage systems useful for the management of nausea and vomiting, such as for the prevention and/or treatment of nausea and vomiting of pregnancy (NVP).

BACKGROUND ART

Nausea and vomiting of pregnancy (NVP), also referred to as "morning sickness," is very common. It afflicts 50% to 80% of pregnant women with varying degrees of severity.

Commonly occurring within the first 4 to 16 weeks of pregnancy, approximately 20% of women will continue to experience NVP for a longer period of time. Some women may suffer from NVP until the end of the pregnancy. Nausea and vomiting can have serious adverse effects. If severe enough, NVP can cause dehydration, with associated salt and vitamin imbalances. These and other effects can be harmful to the health of the woman and the well-being of her baby. In its most severe form, NVP may manifest itself as hyperemesis gravidarum, a potentially life-threatening condition affecting 0.5% to 2% of pregnancies, which is characterized by protracted vomiting, retching, severe dehydration, and weight loss requiring hospitalization.

The delayed release combination of Doxylamine succinate/Pyridoxine HCl (10 mg each), marketed in Canada under the trade-name Diclectin® and in the United States under the trade-name Diclegis®, is the only medication approved in Canada and U.S. for the treatment of NVP. Its safety and effectiveness for the treatment of NVP is recognized by the medical community, and its safety throughout pregnancy has been long established.

Nevertheless, there is a need for the development of novel pharmaceutical compositions, dosage systems and forms for the management of nausea and vomiting, such as in NVP.

The present description refers to a number of documents, the content of which is herein incorporated by reference in their entirety.

SUMMARY OF THE INVENTION

The present invention relates to pharmaceutical compositions and dosage systems, as well as related methods, uses and kits. The pharmaceutical compositions, dosage systems methods, uses and kits may be used for example for the management of nausea and vomiting, such as for the prevention and/or treatment of nausea and vomiting of pregnancy (NVP).

In an aspect, the present invention provides a pharmaceutical dosage system comprising:

(a) from about 5 to about 40 mg of one or more of (i) Doxylamine, (ii) an analog thereof, (iii) a derivative thereof, (iv) a prodrug thereof, (v) a metabolite thereof and (vi) a pharmaceutically acceptable salt of any of (i)-(v);

(b) from about 5 to about 80 mg of one or more of (i) Pyridoxine, (ii) an analog thereof, (iii) a derivative thereof, (iv) a prodrug thereof, (v) a metabolite thereof and (vi) a pharmaceutically acceptable salt of any of (i)-(v); and (c) from about 20 to about 100 mg of one or more compounds of formula (I)

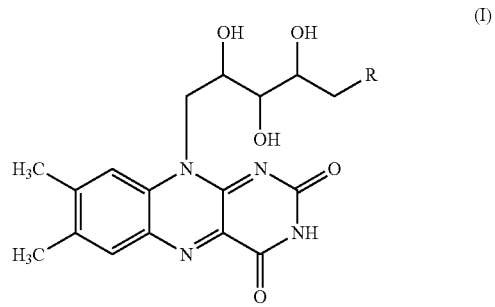

wherein R is a hydroxyl group, a phosphate group or

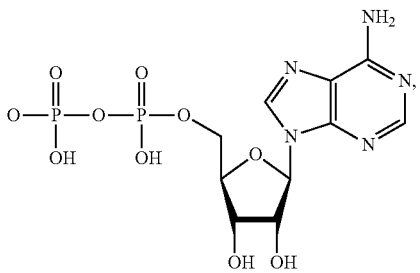

or a pharmaceutically acceptable salt thereof.

In another aspect, the present invention provides a dosage system for alleviating the symptoms of nausea and vomiting of human pregnancy, said system comprising (a) an effective amount of one or more of (i) Doxylamine, (ii) an analog thereof, (iii) a derivative thereof, (iv) a prodrug thereof, (v) a metabolite thereof and (vi) a pharmaceutically acceptable salt of any of (i)-(v);

(b) an effective amount of one or more of (i) Pyridoxine, (ii) an analog thereof, (iii) a derivative thereof, (iv) a prodrug thereof, (v) a metabolite thereof and (vi) a pharmaceutically acceptable salt of any of (i)-(v); and (c) an effective amount of one or more compounds of formula (I)

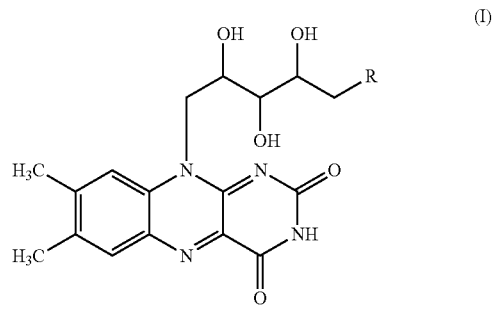

wherein R is a hydroxyl group, a phosphate group or

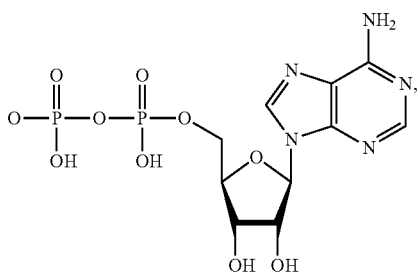

or a pharmaceutically acceptable salt thereof.

In another aspect, the present invention provides a dosage system consisting essentially of:
(a) an effective amount of one or more of (i) Doxylamine, (ii) an analog thereof, (iii) a derivative thereof, (iv) a prodrug thereof, (v) a metabolite thereof and (vi) a pharmaceutically acceptable salt of any of (i)-(v);
(b) an effective amount of one or more of (i) Pyridoxine, (ii) an analog thereof, (iii) a derivative thereof, (iv) a prodrug thereof, (v) a metabolite thereof and (vi) a pharmaceutically acceptable salt of any of (i)-(v); and
(c) an effective amount of one or more compounds of formula (I)

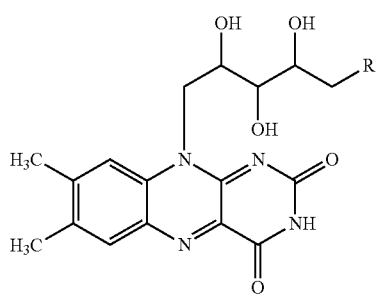

wherein R is a hydroxyl group, a phosphate group or

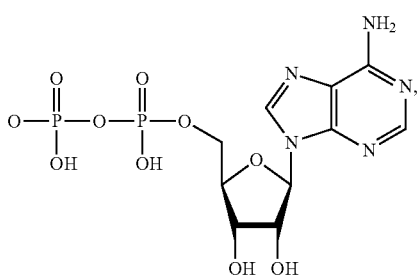

or a pharmaceutically acceptable salt thereof.

In another aspect, the present invention provides a method for alleviating the symptoms of nausea and vomiting of human pregnancy, said method comprising administering to a human subject in need thereof:
(a) an effective amount of one or more of (i) Doxylamine, (ii) an analog thereof, (iii) a derivative thereof, (iv) a prodrug thereof, (v) a metabolite thereof and (vi) a pharmaceutically acceptable salt of any of (i)-(v);
(b) an effective amount of one or more of (i) Pyridoxine, (ii) an analog thereof, (iii) a derivative thereof, (iv) a prodrug thereof, (v) a metabolite thereof and (vi) a pharmaceutically acceptable salt of any of (i)-(v); and
(c) an effective amount of one or more compounds of formula (I)

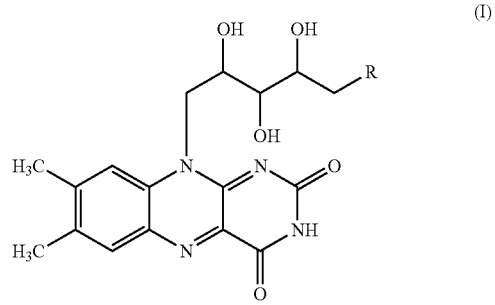

wherein R is a hydroxyl group, a phosphate group or

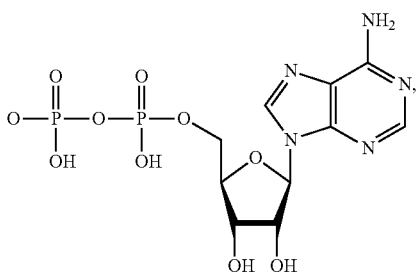

or a pharmaceutically acceptable salt thereof.

In another aspect, the present invention provides the use of:
(a) an effective amount of one or more of (i) Doxylamine, (ii) an analog thereof, (iii) a derivative thereof, (iv) a prodrug thereof, (v) a metabolite thereof and (vi) a pharmaceutically acceptable salt of any of (i)-(v);
(b) an effective amount of one or more of (i) Pyridoxine, (ii) an analog thereof, (iii) a derivative thereof, (iv) a prodrug thereof, (v) a metabolite thereof and (vi) a pharmaceutically acceptable salt of any of (i)-(v); and
(c) an effective amount of one or more compounds of formula (I)

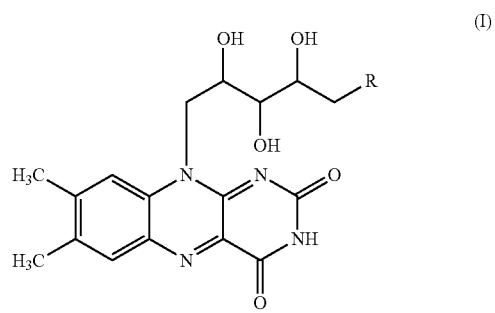

wherein R is a hydroxyl group, a phosphate group or

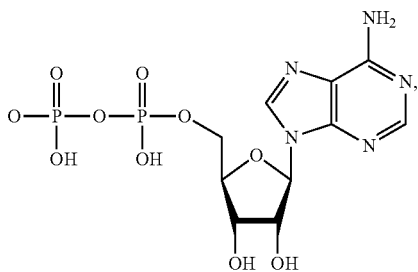

or a pharmaceutically acceptable salt thereof,
for alleviating the symptoms of nausea and vomiting of human pregnancy (NVP).

In another aspect, the present invention provides the use of:
(a) an effective amount of one or more of (i) Doxylamine, (ii) an analog thereof, (iii) a derivative thereof, (iv) a prodrug thereof, (v) a metabolite thereof and (vi) a pharmaceutically acceptable salt of any of (i)-(v);
(b) an effective amount of one or more of (i) Pyridoxine, (ii) an analog thereof, (iii) a derivative thereof, (iv) a prodrug thereof, (v) a metabolite thereof and (vi) a pharmaceutically acceptable salt of any of (i)-(v); and
(c) an effective amount of one or more compounds of formula (I)

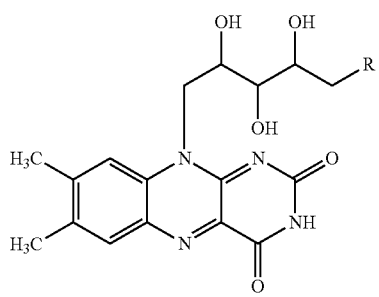

wherein R is a hydroxyl group, a phosphate group or

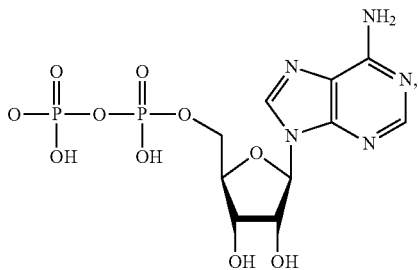

or a pharmaceutically acceptable salt thereof,
for the preparation of a medicament for alleviating the symptoms of NVP.

In another aspect, the present invention provides a composition comprising:
(a) an effective amount of one or more of (i) Doxylamine, (ii) an analog thereof, (iii) a derivative thereof, (iv) a prodrug thereof, (v) a metabolite thereof and (vi) a pharmaceutically acceptable salt of any of (i)-(v);
(b) an effective amount of one or more of (i) Pyridoxine, (ii) an analog thereof, (iii) a derivative thereof, (iv) a prodrug thereof, (v) a metabolite thereof and (vi) a pharmaceutically acceptable salt of any of (i)-(v); and
(c) an effective amount of one or more compounds of formula (I)

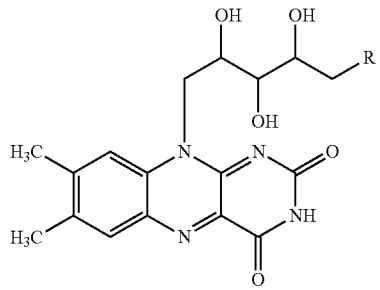

wherein R is a hydroxyl group, a phosphate group or

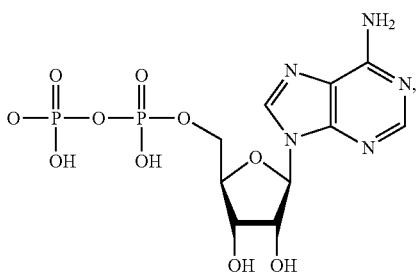

or a pharmaceutically acceptable salt thereof,
for alleviating the symptoms of NVP.

In another aspect, the present invention provides a composition comprising:
(a) an effective amount of one or more of (i) Doxylamine, (ii) an analog thereof, (iii) a derivative thereof, (iv) a prodrug thereof, (v) a metabolite thereof and (vi) a pharmaceutically acceptable salt of any of (i)-(v);
(b) an effective amount of one or more of (i) Pyridoxine, (ii) an analog thereof, (iii) a derivative thereof, (iv) a prodrug thereof, (v) a metabolite thereof and (vi) a pharmaceutically acceptable salt of any of (i)-(v); and
(c) an effective amount of one or more compounds of formula (I)

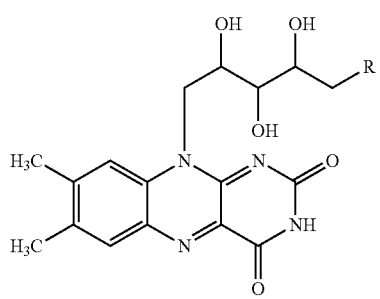

wherein R is a hydroxyl group, a phosphate group or

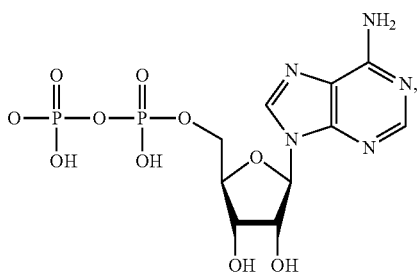

or a pharmaceutically acceptable salt thereof,
for the preparation of a medicament for alleviating the symptoms of NVP.

In an embodiment, R is a hydroxyl group. In another embodiment, R is a phosphate group.

In an embodiment, the above-mentioned system comprises from about 5 to about 35 mg of (i) Doxylamine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises from about 5 to about 30 mg of (i) Doxylamine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises from about 5 to about 20 mg of (i) Doxylamine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises from about 10 to about 20 mg of (i) Doxylamine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises about 20 mg of (i) Doxylamine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises about 10 mg of (i) Doxylamine (ii) an analog thereof, (iii) a derivative thereof, (iv) a prodrug thereof, (v) a metabolite thereof and/or (vi) a pharmaceutically acceptable salt of any of (i)-(v).

In an embodiment, the above-mentioned salt of Doxylamine is Doxylamine succinate.

In an embodiment, the above-mentioned system comprises from about 5 to about 70 mg of (i) Pyridoxine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises from about 5 to about 50 mg of (i) Pyridoxine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises from about 5 to about 30 mg of (i) Pyridoxine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises from about 5 mg to about 20 mg of (i) Pyridoxine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises from about 10 mg to about 20 mg of (i) Pyridoxine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises about 10 mg of (i) Pyridoxine (ii) an analog thereof, (iii) a derivative thereof, (iv) a prodrug thereof, (v) a metabolite thereof and/or (vi) a pharmaceutically acceptable salt of any of (i)-(v).

In a further embodiment, the above-mentioned system comprises about 20 mg of (i) Pyridoxine (ii) an analog thereof, (iii) a derivative thereof, (iv) a prodrug thereof, (v) a metabolite thereof and/or (vi) a pharmaceutically acceptable salt of any of (i)-(v).

In an embodiment, the above-mentioned system comprises Pyridoxine hydrochloride.

In an embodiment, the above-mentioned system comprises at least about 20 mg of said one or more compounds of formula (I) or pharmaceutically acceptable salt thereof.

In an embodiment, the above-mentioned system comprises from about 20 or 25 to about 90 mg of said one or more compounds of formula (I) or pharmaceutically acceptable salt thereof.

In a further embodiment, the above-mentioned system comprises from about 20 or 25 to about 80 mg of said one or more compounds of formula (I) or pharmaceutically acceptable salt thereof.

In a further embodiment, the above-mentioned system comprises from about 20 or 25 to about 60 mg of said one or more compounds of formula (I) or pharmaceutically acceptable salt thereof.

In a further embodiment, the above-mentioned system comprises from about 20 or 25 to about 50 mg of said one or more compounds of formula (I) or pharmaceutically acceptable salt thereof.

In a further embodiment, the above-mentioned system comprises from about 20 or 25 to about 40 mg of said one or more compounds of formula (I) or pharmaceutically acceptable salt thereof.

In a further embodiment, the above-mentioned system comprises from about 30 to about 50 mg of said one or more compounds of formula (I) or pharmaceutically acceptable salt thereof.

In a further embodiment, the above-mentioned system comprises about 30 mg of said one or more compounds of formula (I) or pharmaceutically acceptable salt thereof.

In a further embodiment, the above-mentioned system comprises about 40 mg of said one or more compounds of formula (I) or pharmaceutically acceptable salt thereof.

In a further embodiment, the above-mentioned system comprises about 50, 60, 70, 80 or 90 mg of said one or more compounds of formula (I) or pharmaceutically acceptable salt thereof.

In an embodiment, the above-mentioned (a), (b) and (c) are in the same pharmaceutical composition. In another embodiment, the above-mentioned (a), (b) and (c) are in a plurality of pharmaceutical compositions.

In an embodiment, the above-mentioned system comprises an immediate release component and a delayed release component.

In an embodiment, the above-mentioned immediate release component comprises (a) and (b).

In an embodiment, the above-mentioned delayed release component comprises (a), (b) and (c).

In an embodiment, the above-mentioned system further comprises at least one pharmaceutically acceptable excipient.

In an embodiment, the above-mentioned system comprises one or more oral dosage forms. In a further embodiment, the above-mentioned one or more oral dosage forms are in the form of tablets, pills, capsules, solutions or flowable powders.

In another aspect, the present invention provides a method for alleviating the symptoms of nausea and vomiting in a human subject, said method comprising administering the above-mentioned system to a human subject in need thereof.

In another aspect, the present invention provides the use of the above-mentioned system for alleviating the symptoms of nausea and vomiting in a human subject.

In another aspect, the present invention provides the use of the above-mentioned system for the preparation of a medicament for alleviating the symptoms of nausea and vomiting in a human subject.

In another aspect, the present invention provides the above-mentioned system for alleviating the symptoms of nausea and vomiting in a human subject.

In another aspect, the present invention provides the above-mentioned system for the preparation of a medicament for alleviating the symptoms of nausea and vomiting in a human subject.

In another aspect, the present invention provides a method for alleviating the symptoms of nausea and vomiting of human pregnancy, said method comprising administering the above-mentioned system to a human subject in need thereof.

In another aspect, the present invention provides the use of the above-mentioned system for alleviating the symptoms of nausea and vomiting of human pregnancy (NVP).

In another aspect, the present invention provides the use of the above-mentioned system for the preparation of a medicament for alleviating the symptoms of NVP.

In another aspect, the present invention provides the above-mentioned system for alleviating the symptoms of nausea and vomiting of human pregnancy (NVP).

In another aspect, the present invention provides the above-mentioned system for the preparation of a medicament for alleviating the symptoms of nausea and vomiting of human pregnancy (NVP).

Other objects, advantages and features of the present invention will become more apparent upon reading of the following non-restrictive description of specific embodiments thereof, given by way of example only with reference to the accompanying drawings.

DISCLOSURE OF INVENTION

In the studies described herein, the present inventors have shown that a dosage system comprising flavin mononucleotide (FMN, also known as riboflavin-5-phosphate or R5P), a metabolite of riboflavin, together with a combination of Doxylamine and Pyridoxine, exhibits an improved pharmacokinetics profile relative to a dosage system comprising a combination of Doxylamine and Pyridoxine (and/or metabolites thereof) but lacking FMN. More particularly, the use of FMN was shown to result in improvement in the pharmacokinetics (e.g., a faster time of appearance in the plasma) of the metabolite Pyridoxal-5'-Phosphate (PLP). It has been demonstrated that plasma levels of doxylamine and PLP are inversely correlated with the severity of the symptoms of NPV (FIG. 1), providing evidence that PLP is an active metabolite of Pyridoxine, and also providing sound prediction that improved pharmacokinetics will improve efficacy in the reduction of the symptoms of NVP. In contrast to administration of FMN, administration of PLP (or Pyridoxal (PYL), another metabolite of Pyridoxine) together with a combination of Doxylamine and Pyridoxine, did not result in such improvement (e.g., faster time of appearance of PLP). It was thus determined that the administration of FMN results in improvement in the pharmacokinetics of PLP, which is not obtained by direct administration of PLP itself.

Figure 5:
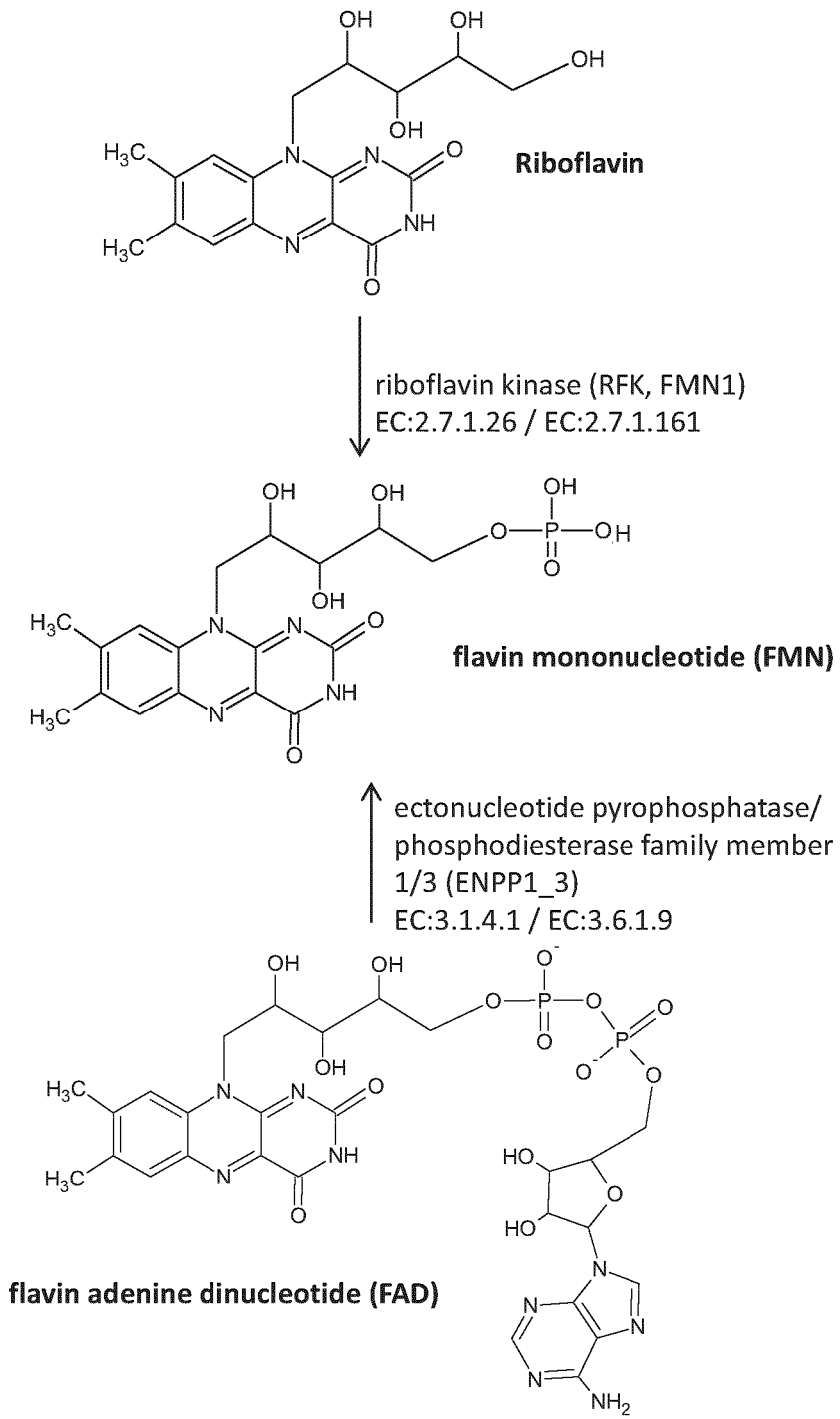
FIG. 5 shows the metabolic interrelationship between riboflavin, flavin mononucleotide (FMN) and flavin adenine dinucleotide (FAD). Riboflavin may be enzymatically converted to FMN through the catalytic activity of a riboflavin kinase (in the presence of ATP), and FAD may be enzymatically converted to FMN by an ectonucleotide pyrophosphatase/phosphodiesterase (ENPP1_3).

Riboflavin is the precursor of the cofactors FMN and flavin adenine dinucleotide (FAD). FAD and FMN serve as cofactors for certain enzymes, such as reduction-oxidation enzymes that are involved in energy metabolism. FMN is the principal form in which riboflavin is found in cells and tissues. The metabolic interrelationship between riboflavin, flavin mononucleotide (FMN) and flavin adenine dinucleotide (FAD) is depicted in FIG. 5. Riboflavin is enzymatically converted to FMN through the catalytic activity of a riboflavin kinase (in the presence of ATP), and FAD is enzymatically converted to FMN by an ectonucleotide pyrophosphatase/phosphodiesterase (ENPP1_3). Thus, FMN may be administered directly, or indirectly via administration of the precursor riboflavin or the metabolite FAD, which are then enzymatically converted to FMN under normal metabolic conditions.

Thus, the present invention relates to a combination of three biologically active agents, (1) a Doxylamine component (or compound), i.e. one or more of (i) Doxylamine, (ii) an analog thereof, (iii) a derivative thereof, (iv) a prodrug thereof, (v) a metabolite thereof and (vi) a salt of any of (i)-(v), (2) a Pyridoxine component (or compound), i.e. one or more of (i) Pyridoxine, (ii) an analog thereof, (iii) a derivative thereof, (iv) a prodrug thereof, (v) a metabolite thereof and (vi) a salt of any of (i)-(v), and (3) a riboflavin compound, i.e. riboflavin, or a cofactor thereof (FMN or FAD) or a salt thereof, and the use of such combination in the management of nausea and vomiting, such as for the prevention and/or treatment of NVP. "Biologically active agent" as used herein means that the compound itself, or a metabolite thereof, exhibits one or more biological effects on certain cells when administered to a subject.

Accordingly, in a first aspect, the present invention provides a dosage system comprising:

(a) from about 5 to about 40 mg of a Doxylamine component (or compound), i.e. one or more of (i) Doxylamine, (ii) an analog thereof, (iii) a derivative thereof, (iv) a prodrug thereof, (v) a metabolite thereof and (vi) a salt of any of (i)-(v);

(b) from about 5 to about 80 mg of a Pyridoxine component (or compound), i.e. one or more of (i) Pyridoxine, (ii) an analog thereof, (iii) a derivative thereof, (iv) a prodrug thereof, (v) a metabolite thereof and (vi) a salt of any of (i)-(v); and (c) at least about 20 mg of one or more compounds of formula (I)

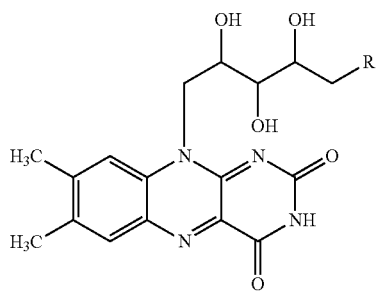

wherein R is a hydroxyl group (OH), a phosphate group ($PO_4^{2-}$ or $HPO_4^-$ or $H_2PO_4$) or

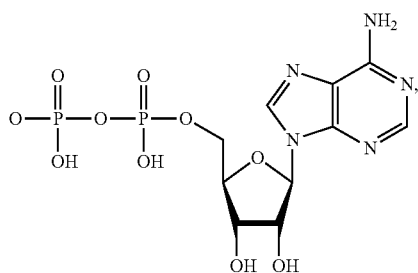

or a pharmaceutically acceptable salt thereof.

In another aspect, the present invention provides a dosage system comprising:

(a) from about 5 to about 40 mg of a Doxylamine component (or compound), i.e. one or more of (i) Doxylamine, (ii) an analog thereof, (iii) a derivative thereof, (iv) a prodrug thereof, (v) a metabolite thereof and (vi) a salt of any of (i)-(v);

(b) from about 5 to about 80 mg of a Pyridoxine component (or compound), i.e. one or more of (i) Pyridoxine, (ii) an analog thereof, (iii) a derivative thereof, (iv) a prodrug thereof, (v) a metabolite thereof and (vi) a salt of any of (i)-(v); and (c) from about 20 to about 100 mg of one or more compounds of formula (I)

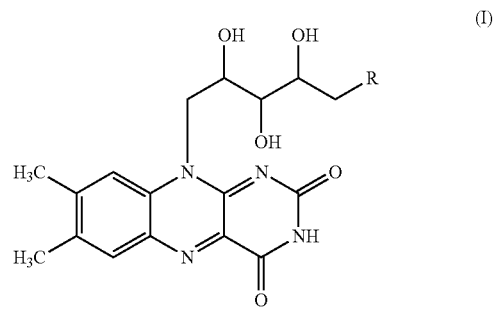

wherein R is a hydroxyl group (OH), a phosphate group ($PO_4^{2-}$ or $HPO_4^-$ or $H_2PO_4$) or

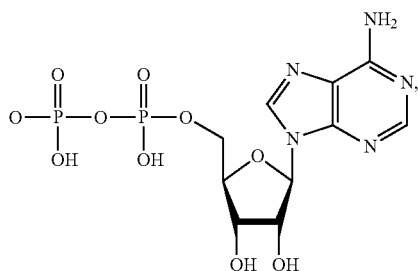

or a pharmaceutically acceptable salt thereof.

In another aspect, the present invention provides a dosage system for alleviating the symptoms of nausea and vomiting of human pregnancy, said system comprising (a) an effective amount of a Doxylamine component (or compound), i.e. one or more of (i) Doxylamine, (ii) an analog thereof, (iii) a derivative thereof, (iv) a prodrug thereof, (v) a metabolite thereof and (vi) a salt of any of (i)-(v);

(b) an effective amount of a Pyridoxine component (or compound), i.e. one or more of (i) Pyridoxine, (ii) an analog thereof, (iii) a derivative thereof, (iv) a prodrug thereof, (v) a metabolite thereof and (vi) a salt of any of (i)-(v); and (c) an effective amount of one or more compounds of formula (I)

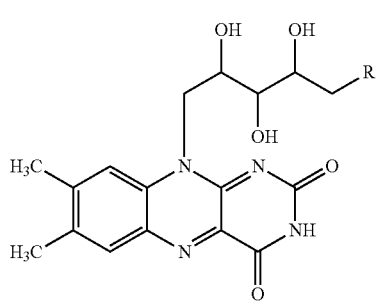
(I)

wherein R is a hydroxyl group (OH), a phosphate group ($PO_4^{2-}$ or $HPO_4^-$ or $H_2PO_4$), or

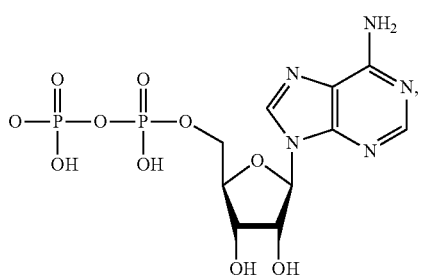

or a pharmaceutically acceptable salt thereof.

In another aspect, the present invention provides a dosage system consisting essentially of:

(a) an effective amount of a Doxylamine component (or compound), i.e. one or more of (i) Doxylamine, (ii) an analog thereof, (iii) a derivative thereof, (iv) a prodrug thereof, (v) a metabolite thereof and (vi) a salt of any of (i)-(v);

(b) an effective amount of a Pyridoxine component (or compound), i.e. one or more of (i) Pyridoxine, (ii) an analog thereof, (iii) a derivative thereof, (iv) a prodrug thereof, (v) a metabolite thereof and (vi) a salt of any of (i)-(v); and (c) an effective amount of one or more compounds of formula (I)

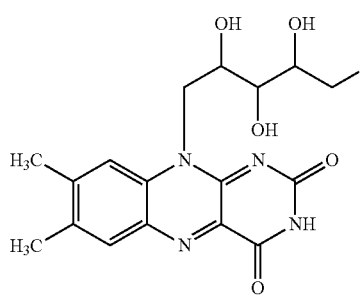
(I)

wherein R is a hydroxyl group (OH), a phosphate group ($PO_4^{2-}$ or $HPO_4^-$ or $H_2PO_4$), or

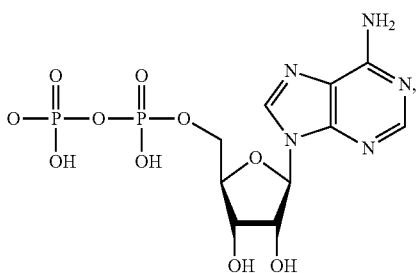

or a pharmaceutically acceptable salt thereof; and (d) one or more pharmaceutically acceptable excipients.

In another aspect, the present invention provides a dosage system consisting of:

(a) an effective amount of a Doxylamine component (or compound), i.e. one or more of (i) Doxylamine, (ii) an analog thereof, (iii) a derivative thereof, (iv) a prodrug thereof, (v) a metabolite thereof and (vi) a salt of any of (i)-(v);

(b) an effective amount of a Pyridoxine component (or compound), i.e. one or more of (i) Pyridoxine, (ii) an analog thereof, (iii) a derivative thereof, (iv) a prodrug thereof, (v) a metabolite thereof and (vi) a salt of any of (i)-(v);

(c) an effective amount of one or more compounds of formula (I)

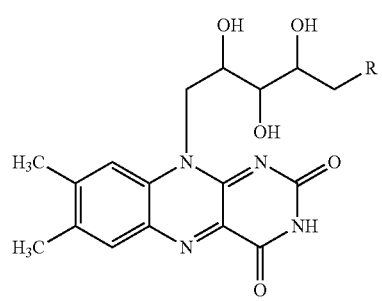
(I)

wherein R is a hydroxyl group (OH), a phosphate group ($PO_4^{2-}$ or $HPO_4^-$ or $H_2PO_4$),

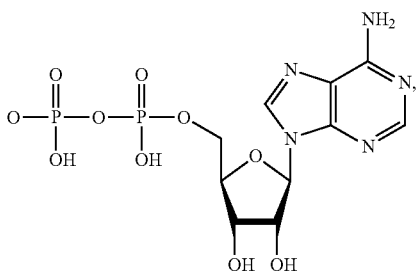

or a pharmaceutically acceptable salt thereof; and (d) one or more pharmaceutically acceptable excipients.

In another aspect, the present invention provides a dual release dosage system comprising (a) an effective amount of a Doxylamine component, i.e. one or more of (i) Doxylamine, (ii) an analog thereof, (iii) a derivative thereof, (iv) a prodrug thereof, (v) a metabolite thereof and (vi) a salt of any of (i)-(v); (b) an effective amount of a Pyridoxine component, i.e. one or more of (i) Pyridoxine, (ii) an analog thereof, (iii) a derivative thereof, (iv) a prodrug thereof, (v) a metabolite thereof and (vi) a salt of any of (i)-(v), and (c) an effective amount of one or more compounds of formula (I)

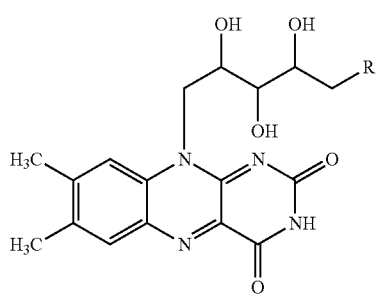

wherein R is a hydroxyl group (OH), a phosphate group ($PO_4^{2-}$ or $HPO_4^-$ or $H_2PO_4$), or

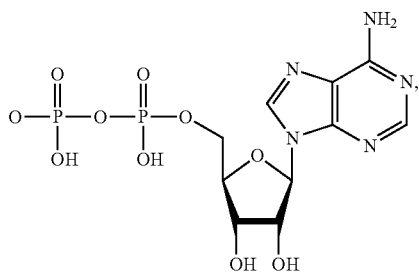

said dual release oral dosage system comprising:
(A) an immediate release component comprising (a), (b) and/or (c): and
(B) a delayed release component comprising (a), (b) and/or (c):
wherein the immediate release component is for effecting release of (a), (b) and/or (c) comprised therein, which begins prior to release of (a), (b) and/or (c) from the delayed release component, within the gastrointestinal tract.

Throughout the present specification, the term "(a)" or "ingredient (a)" is used to refer to the "Doxylamine component" or "Doxylamine compound", the term "(b)" or "ingredient (b)" is used to refer to the "Pyridoxine component" or "Pyridoxine compound", and the term "(c)" or "ingredient (c)" is used to refer to the compound of formula I or salt thereof.

The term "Doxylamine component" (or "Doxylamine compound") as used herein refers to Doxylamine, Doxylamine analogs, derivatives, prodrugs, metabolites and/or salts. The term "Pyridoxine component" (or "Pyridoxine compound") as used herein refers to Pyridoxine, Pyridoxine analogs, derivatives, prodrugs, metabolites and/or salts.

The term "analog" or "derivative" as used herein refers to a different compound having a structure similar to that of the "parent" compound (e.g., Doxylamine or Pyridoxine) but differing from the parent compound in structure (e.g., replacement of one or more atoms by an atom of a different element, presence or absence of a particular group, etc.). An analog/derivative typically exhibits an overall biological effect that is similar to that of the "parent" compound but may differ in one or more physicochemical and/or pharmacokinetic properties (potency, stability, solubility, absorption, in vivo half-life, in vivo distribution, etc.).

"Prodrug" as used herein refers to a compound for administration (which is e.g., in an inactive, or significantly less active form) in a form that, following administration, undergoes chemical conversion by metabolic processes to be transformed into a compound to effect the desired pharmacological activity (e.g., to become an active, or more active, pharmacological agent).

"Metabolite" as used herein refers to a compound resulting from a biochemical conversion of a first compound by metabolic processes/pathways in vivo. A metabolite may differ in one or more physicochemical and/or pharmacokinetic properties (potency, stability, solubility, absorption, in vivo half-life, in vivo distribution, etc.) as compared to the first compound (which may be a prodrug or an active agent). If its structure is known, such a metabolite can be prepared in vitro and administered directly to a subject to exert a biological effect. A given metabolite may itself be metabolized through metabolic processes/pathways, thus resulting in one or more further metabolites that may differ in more or more physicochemical and/or pharmacokinetic properties as compared to the "first" metabolite.

The term "about" is used to indicate that a value includes an inherent variation of error for the device or the method being employed to determine the value, or encompass values close to the recited values, for example within 10% of the recited values (or of the extremities of a recited range of values).

In an embodiment, the Doxylamine compound is Doxylamine.

Pyridoxine analogs, derivatives, prodrugs, metabolites and salts include, for example, pharmaceutically acceptable esters or amines of Pyridoxine, Pyridoxine hydrochloride (Pyridoxine-HCl), Pyridoxine phosphate, Pyridoxal, Pyridoxal phosphate, Pyridoxal calcium phosphate, Pyridoxal hydrochloride, Pyridoxamine, Pyridoxamine 5-phosphate or Pyridoxamine dihydrochloride.

In an embodiment, the Pyridoxine compound is a compound of formula II,

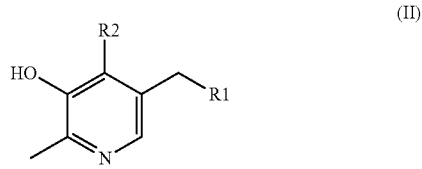

wherein
R1 is a hydroxyl (OH) or phosphate ($PO_4^{2-}$ or $HPO_4^-$ or $H_2PO_4$) group; and
R2 is $CH_2OH$, CHO, or $CH_2NH_2$
or a pharmaceutically acceptable salt thereof.

In an embodiment, the Pyridoxine compound is Pyridoxine (PYR), Pyridoxine 5-phosphate (PYP), Pyridoxal (PYL), Pyridoxal 5-phosphate (PLP), Pyridoxamine (PYM), Pyridoxamine 5-phosphate (PMP), and/or a pharmaceutically acceptable salt of PYR, PYP, PYL, PLP, PYM and/or PMP.

As used herein the term "pharmaceutically acceptable salt" refers to a salt of a compound (an active ingredient) that retains the biological activity of the parent compound, and which is not biologically or otherwise undesirable, i.e., is a type of salt and/or is for use in an amount which is not toxic to the subject. In the case of a pregnant human female subject, the pharmaceutically acceptable salt is in a concentration that is not toxic to the embryo or fetus, (i.e., a pharmaceutical salt which is acceptable for administration to a pregnant female) and not contraindicated for use in human pregnancy. Thus, in dosage forms for administration to pregnant subjects, pharmaceutically acceptable salts that have teratogenic properties are excluded.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid. In an embodiment, the pharmaceutically acceptable salt of Doxylamine is Doxylamine succinate.

In another aspect, the present invention provides a dosage system comprising:
(i) from about 5 to about 40 mg of a Doxylamine succinate;
(ii) from about 5 to about 80 mg of a Pyridoxine hydrochloride (Pyridoxine HCl); and
(iii) from about 20 to about 100 mg of one or more compounds of formula (I)

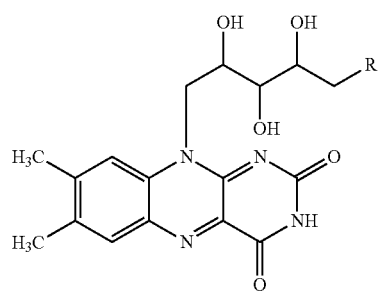

wherein R is a hydroxyl group (OH), a phosphate group ($PO_4^{2-}$ or $HPO_4^-$ or $H_2PO_4$) or

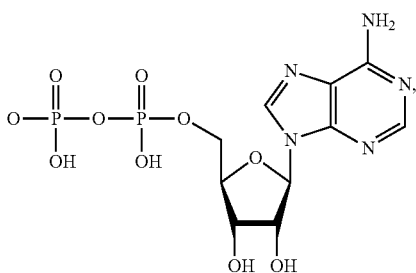

or a pharmaceutically acceptable salt thereof.

In another aspect, the present invention provides a dosage system for alleviating the symptoms of nausea and vomiting of human pregnancy, said system comprising
(i) Doxylamine succinate;
(ii) Pyridoxine HCl; and
(iii) one or more compounds of formula (I)

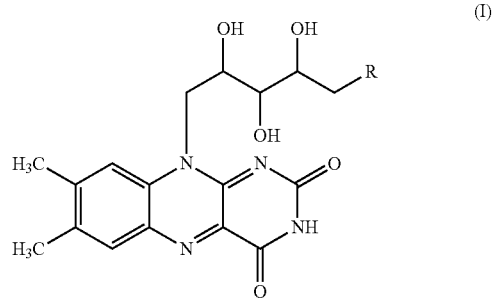

wherein R is a hydroxyl group (OH), a phosphate group ($PO_4^{2-}$ or $HPO_4^-$ or $H_2PO_4$), or

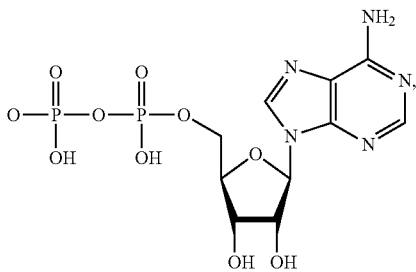

or a pharmaceutically acceptable salt thereof.

In another aspect, the present invention provides a dosage system consisting essentially of:
(i) Doxylamine succinate;
(ii) Pyridoxine HCl; and
(iii) one or more compounds of formula (I)

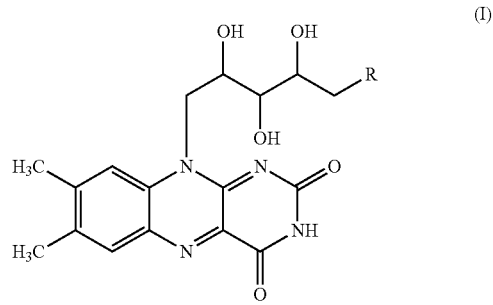

wherein R is a hydroxyl group (OH), a phosphate group ($PO_4^{2-}$ or $HPO_4^-$ or $H_2PO_4$), or

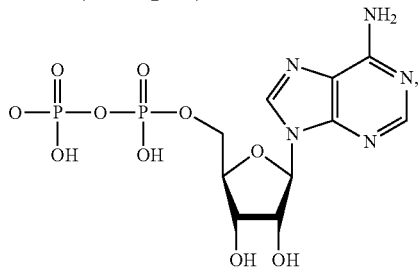

or a pharmaceutically acceptable salt thereof; and
(iv) one or more pharmaceutically acceptable excipients.

In another aspect, the present invention provides a dosage system consisting of:
(i) Doxylamine succinate;
(ii) Pyridoxine HCl; and
(iii) one or more compounds of formula (I)

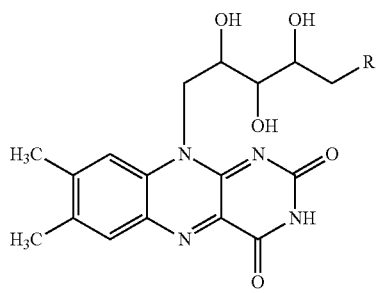

(I)

wherein R is a hydroxyl group (OH), a phosphate group ($PO_4^{2-}$ or $HPO_4^-$ or $H_2PO_4$), or

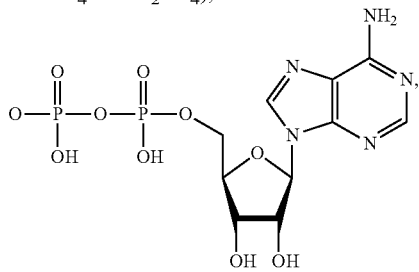

or a pharmaceutically acceptable salt thereof; and
(iv) one or more pharmaceutically acceptable excipients.

In another aspect, the present invention provides a dual release dosage system comprising (i) Doxylamine succinate; (ii) Pyridoxine HCl and (iii) one or more compounds of formula (I)

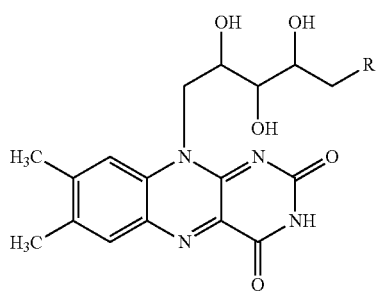

(I)

wherein R is a hydroxyl group (OH), a phosphate group ($PO_4^{2-}$ or $HPO_4^-$ or $H_2PO_4$), or

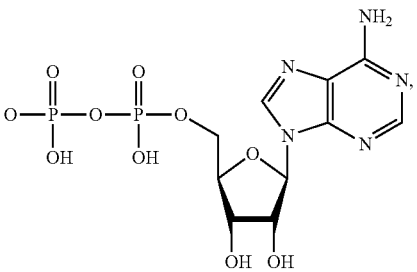

said dual release oral dosage system comprising:
(A) an immediate release component comprising (i), (ii) and/or (iii): and
(B) a delayed release component comprising (i), (ii) and/or (iii):
wherein the immediate release component is for effecting release of (i), (ii) and/or (iii), which begins prior to release of (i), (ii) and/or (iii) from the delayed release component, within the gastrointestinal tract.

In an embodiment, the above-mentioned system provides a maximum daily dosage of the Doxylamine, analog thereof, derivative thereof, prodrug thereof, metabolite thereof and/or salt thereof of about 30 to about 40 mg, in a further embodiment about 30, 35 or 40 mg.

In an embodiment, the above-mentioned system provides a daily dosage of the Doxylamine, analog thereof, derivative thereof, prodrug thereof, metabolite thereof and/or salt thereof of about 5 mg to about 40 mg, in a further embodiment form about 10 to about 30 mg, for example about 10, 15, 20, 25, or 30 mg. In an embodiment, the above-mentioned system provides a daily dosage of the Doxylamine, analog thereof, derivative thereof, prodrug thereof, metabolite thereof and/or salt thereof of about 40 mg.

In an embodiment, the above-mentioned system provides a maximum daily dosage of the Pyridoxine, analog thereof, derivative thereof, prodrug thereof, metabolite thereof and/or salt thereof, of about 60 to about 80 mg, in a further embodiment about 80 mg.

In an embodiment, the above-mentioned system provides a daily dosage of the Pyridoxine, analog thereof, derivative thereof, prodrug thereof, metabolite thereof and/or salt thereof, of about 5 mg to about 80 mg, for example, from about 5, 10, 15, 20, 25 to about 30, 35, 40, 45, 50, 55, 60, 65, 70, 75 or 80 mg. In an embodiment, the above-mentioned system provides a daily dosage of the Pyridoxine, analog thereof, derivative thereof, prodrug thereof, metabolite thereof and/or salt thereof, of about 20 to 60 mg, in a further embodiment about 40 mg.

In an embodiment, the above-mentioned system provides a daily dosage of the compound of formula I or salt thereof of about 40 mg to about 200 mg, for example, from about 40, 45, 50, 55 or 60 to about 80, 85, 90, 95, 100, 110, 120, 130, 140, 150 or 160 mg. In an embodiment, the above-mentioned system provides a daily dosage of the compound of formula I or salt thereof of about 40 to 100 mg, in a further embodiment about 80 mg.

In an embodiment, the above-mentioned system is a once-a-day system. In another embodiment, the above-mentioned system is a twice-a-day system.

Dosage

Dosage regimens may be adjusted to provide the optimum prophylactic/therapeutic response, via administration of effective amount (e.g., a prophylactically and/or therapeutically effective amount) of the ingredients (a), (b) and (c).

An effective amount is one in which any toxic or detrimental effects of the ingredients (a), (b) and (c) are outweighed by the prophylactic or therapeutic beneficial effects (e.g., alleviation of one or more symptoms of NVP). In an embodiment, for ingredient (c), the beneficial effect comprises inducing a faster increase in the plasma level of PLP in a subject (relative to a control subject not administered with ingredient (c)). For administration to a pregnant human female subject, the effective amount of the active agents is such that it is not toxic to the embryo or fetus.

In an embodiment, the dosage system comprises about 40 mg or less (e.g., about 25, 20, 15 mg or less) of the Doxylamine, analog thereof, derivative thereof, prodrug thereof, metabolite thereof and/or salt thereof. In an embodiment, the dosage system comprises about 30 mg or less (e.g., about 25, 20, 15 mg or less) of the Doxylamine, analog thereof, derivative thereof, prodrug thereof, metabolite thereof and/or salt thereof, in embodiments between about 5, 6, 7, 8, 9, 10, 11, 12, 13, 14, 15 to about 16, 17, 18, 19, 20, 21, 22, 23, 24, 25, 26, 27, 28, 29 or 30 mg. In an embodiment, the dosage system comprises about 5, 6, 7, 8, 9, 10, 11, 12, 13, 14, 15, 16, 17, 18, 19 or 20 mg of the Doxylamine, analog thereof, derivative thereof, prodrug thereof, metabolite thereof and/or salt thereof (e.g., Doxylamine succinate). In an embodiment, the dosage system comprises Doxylamine or a salt thereof, in a further embodiment Doxylamine succinate.

In an embodiment, the dosage system comprises about 80 mg or less (e.g., about 75, 70, 65, 60, 55, 50 mg or less) of the Pyridoxine, analog thereof, derivative thereof, prodrug thereof, metabolite thereof and/or salt thereof, in embodiments between about 0.5, 1, 5, 10, 15, 20, 25, 30 mg to about 35, 40, 45, 50, 55, 60, 65, 70, 75 or 80 mg. In an embodiment, the dosage system comprises about 5, 6, 7, 8, 9, 10, 11, 12, 13, 14, 15, 16, 17, 18, 19, or 20 mg of the Pyridoxine, analog thereof, derivative thereof, prodrug thereof, metabolite thereof and/or salt thereof (e.g., Pyridoxine, PYL, PYP, PLP, PYM and/or PMP). In an embodiment, the dosage system comprises Pyridoxine or a salt thereof, in a further embodiment Pyridoxine-HCl.

In an embodiment, the dosage system comprises at least about 20 mg of the compound of formula I or salt thereof. In an embodiment, the dosage system comprises at least about 21, 22, 23, 24, 25, 26, 27, 28, 29 or 30 mg of the compound of formula I or salt thereof. In an embodiment, the dosage system comprises about 100 mg or less of the compound of formula I or salt thereof. In another embodiment, the dosage system comprises about 95 mg or less of the compound of formula I or salt thereof. In another embodiment, the dosage system comprises about 90 mg or less of the compound of formula I or salt thereof. In another embodiment, the dosage system comprises about 80 mg or less (e.g., about 75, 70, 65, 60, 55, 50 mg or less) of the compound of formula I or salt thereof, in embodiments between about 20, 25, 30 mg to about 35, 40, 45, 50, 55, 60, 65, 70, 75 or 80 mg. In an embodiment, the dosage system comprises about 20, 22, 24, 26, 28, 30, 32, 34, 36, 38, 40, 42, 44, 46, 48 or 50 mg of the one or more compounds of formula I or salt thereof. In an embodiment, the dosage system comprises a compound of formula I wherein R is OH, or a salt thereof.

Excipients

Biologically active ingredients (a), (b) and (c) may be formulated with one or more pharmaceutically acceptable excipients. An "excipient," as used herein, has its normal meaning in the art and is any ingredient of a dosage form (e.g., an oral dosage form) that is not a biologically active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. In the case of a pregnant human female subject, the pharmaceutically acceptable excipient is also not toxic to the embryo or fetus, i.e., a pharmaceutical excipient suitable for administration to a pregnant female (i.e., based on the type and/or amount of such an excipient). Thus, in dosage forms for administration to pregnant subjects, pharmaceutically acceptable excipients that have teratogenic properties and/or that are contraindicated for use in pregnancy are excluded. Excipients are well known in the art, and the present system is not limited in these respects. See, for example, Remington's Pharmaceutical Sciences, 18$^{th}$ Edition, A. Gennaro, Ed., Mack Pub. Co. (Easton, Pa., 1990), Chapters 88-91. In certain embodiments, one or more formulations of the dosage form include excipients, including for example and without limitation, one or more binders (binding agents), thickening agents, surfactants, diluents, release-delaying agents, colorants, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill in the art will also recognize, these terms are not necessarily mutually exclusive.

Useful diluents, e.g., fillers, employable in such formulations may include, for example and without limitation, dicalcium phosphate, calcium diphosphate, calcium carbonate, calcium sulfate, lactose, cellulose, kaolin, sodium chloride, starches, powdered sugar, colloidal silicon dioxide, titanium oxide, alumina, talc, colloidal silica, microcrystalline cellulose, silicified micro crystalline cellulose and combinations thereof. Fillers that can add bulk to tablets with minimal drug dosage to produce tablets of adequate size and weight include croscarmellose sodium NF/EP (e.g., Ac-Di-Sol); anhydrous lactose NF/EP (e.g., Pharmatose™ DCL 21); and/or povidone USP/EP. In an embodiment, the diluent or filler is microcrystalline cellulose.

Binder materials employable in such formulations may include, for example and without limitation, starches (including corn starch and pregelatinized starch), gelatin, sugars (including sucrose, glucose, dextrose and lactose), polyethylene glycol (PEG), povidone, waxes, and natural and synthetic gums, e.g., acacia sodium alginate, polyvinylpyrrolidone, cellulosic polymers (e.g., hydroxypropyl cellulose, hydroxypropyl methylcellulose, methyl cellulose, hydroxyethyl cellulose, carboxymethylcellulose, colloidal silicon dioxide NF/EP (e.g., Cab-O-Sil™ M5P), Silicified Microcrystalline Cellulose (SMCC), e.g., Silicified microcrystalline cellulose NF/EP (e.g., Prosolv™ SMCC 90), and silicon dioxide, mixtures thereof, and the like), veegum, and combinations thereof.

Useful lubricants employable in such formulations may include, for example, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc and, zinc stearate, glyceryl behapate, magnesium lauryl sulfate, boric acid, sodium benzoate, sodium acetate, sodium benzoate/sodium acetate (in combination), DL leucine, calcium stearate, sodium stearyl fumarate, mixtures thereof, and the like. In an embodiment, the lubricant is magnesium stearate.

Bulking agents employable in these compositions may include, for example: microcrystalline cellulose, for example, AVICEL® (FMC Corp.) or EMCOCEL® (Mendell Inc.), which also has binder properties; dicalcium phosphate, for example, EMCOMPRESS® (Mendell Inc.); calcium sulfate, for example, COMPACTROL® (Mendell Inc.); and starches, for example, Starch 1500; and polyethylene glycols (CARBOWAX®).

Suitable disintegrating or dissolution promoting agents employable in such formulations may include, but are not limited to: starches, clays, celluloses, alginates, gums, crosslinked polymers, colloidal silicon dioxide, osmogens, mixtures thereof, and the like, such as crosslinked sodium carboxymethyl cellulose (AC-DI-SOLE)), sodium croscarmelose, sodium starch glycolate (EXPLOTAB®, PRIMO JEL®) crosslinked polyvinylpolypyrrolidone (PLASONE-XL®), sodium chloride, sucrose, lactose, as well as polyols/sugar alcohols such as mannitol and sorbitol. In an embodiment, the disintegrating agent is sodium croscarmelose.

Antiadherents and glidants employable in such formulations may include talc, starches (e.g., cornstarch), celluloses, silicon dioxide, sodium lauryl sulfate, colloidal silica dioxide, and metallic stearates, among others.

Examples of silica flow conditioners include colloidal silicon dioxide, magnesium aluminum silicate and guar gum. In an embodiment, the silica flow conditioner is silicon dioxide.

Suitable surfactants employable in such formulations include pharmaceutically acceptable non-ionic, ionic and anionic surfactants. An example of a surfactant is sodium lauryl sulfate. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, triethanolamine oleate, etc. If desired, flavoring, coloring and/or sweetening agents may be added as well.

Examples of stabilizing agents include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol. In an embodiment, the stabilizing agent is magnesium trisilicate.

Optionally, a thickening agent can be added to provide the dosage form (e.g., tablet) with an accurately timed disintegration behavior. The dosage form optionally disintegrates at a rate which is sufficiently slow to permit it to be swallowed easily, but fast enough to give an excellent suspension in water within 60 seconds. The thickening agent can be for example talc USP/EP, a natural gum, such as guar gum or gum arabic, or a cellulose derivative such as microcrystalline cellulose NF/EP (e.g., Avicel™ PH 102), methylcellulose, ethylcellulose or hydroxyethylcellulose. A useful thickening agent is hydroxypropyl methylcellulose, an adjuvant which is available in various viscosity grades.

Similarly, suitable plasticizers employable in such formulations include: acetylated monoglycerides; alkyl citrates; triethyl citrate (TEC); acetyl triethyl citrate (ATEC; higher boiling point and lower volatility than TEC); tributyl citrate (TBC); acetyl tributyl citrate (ATBC; compatible with PVC and vinyl chloride copolymers); trioctyl citrate (TOC; also used for gums and controlled release medicines); acetyl trioctyl citrate (ATOC); Trihexyl citrate (THC; compatible with PVC, also used for controlled release medicines); acetyl trihexyl citrate (ATHC; compatible with PVC); butyryl trihexyl citrate (BTHC, trihexyl o-butyryl citrate; compatible with PVC); trimethyl citrate (TMC; compatible with PVC); alkyl sulphonic acid phenyl ester, polyethylene glycol (PEG), PlasACRYL® (20% emulsion of mono and di-glycerides (GMS) and plasticizer (triethyl citrate)) or any combination thereof. Optionally, the plasticizer can comprise triethyl citrate NF/EP.

In embodiments, the above-mentioned dosage system further comprises: a filler or binder, a disintegrating or dissolution promoting agent, a lubricant, a silica flow conditioner and a stabilizing agent. In an embodiment, the filler or binder is microcrystalline cellulose. In an embodiment, the disintegrating or dissolution promoting agent is sodium croscarmellose. In an embodiment, the lubricant is magnesium stearate. In an embodiment, the silica flow conditioner is silicon dioxide. In an embodiment, the stabilizing agent is magnesium trisilicate.

Immediate and Delayed Release

In an embodiment, the dosage system comprises an immediate release component and a delayed release component (dual release dosage system).

In an embodiment, the immediate release component and the delayed release component comprise the same Doxylamine, analog thereof, derivative thereof, prodrug thereof, metabolite thereof or salt thereof (or the same combination of Doxylamine, analog thereof, derivative thereof, prodrug thereof, metabolite thereof and/or salt thereof). In another embodiment, the immediate release component and the delayed release component comprise different Doxylamine, analog thereof, derivative thereof, prodrug thereof, metabolite thereof or salt thereof (or a different combination of Doxylamine, analog thereof, derivative thereof, prodrug thereof, metabolite thereof and/or salt thereof). In an embodiment, the immediate release component and/or the delayed release component comprise only one of Doxylamine, an analog thereof, a derivative thereof, a prodrug thereof, a metabolite thereof or a salt thereof. In an embodiment, the immediate release component and/or the delayed release component comprise Doxylamine succinate. In an embodiment, only the immediate release component comprises Doxylamine, an analog thereof, a derivative thereof, a prodrug thereof, a metabolite thereof and/or a salt thereof. In another embodiment, only the delayed release component comprises Doxylamine, an analog thereof, a derivative thereof, a prodrug thereof, a metabolite thereof and/or a salt thereof.

In an embodiment, the above-mentioned immediate release component and/or delayed release component comprise Pyridoxine (PYR) and/or a further ingredient, such as one or more metabolites of PYR, such as PYP, PYL, PLP, PYM and/or PMP, or a pharmaceutically acceptable salt thereof. In an embodiment, the immediate release component and/or the delayed release component comprise Pyridoxal. In an embodiment, the pharmaceutically acceptable salt of Pyridoxine is Pyridoxine HCl. In an embodiment, the immediate release component and the delayed release component comprise the same Pyridoxine, metabolite thereof or salt thereof (or the same combination of Pyridoxine, metabolite thereof and/or salt thereof). In another embodiment, the immediate release component and the delayed release component comprise a different Pyridoxine, prodrug, metabolite thereof or salt thereof (or a different combination of Pyridoxine, prodrug thereof and/or metabolite thereof and/or salt thereof). In an embodiment, only the immediate release component comprises (i) Pyridoxine, (ii) an analog thereof, (iii) a derivative thereof, (iv) a prodrug thereof, (v) a metabolite thereof and/or (vi) a salt of any of (i)-(v). In another embodiment, only the delayed release component comprises (i) Pyridoxine, (ii) an analog thereof, (iii) a derivative thereof, (iv) a prodrug thereof, (v) a metabolite thereof and/or (vi) a salt of any of (i)-(v). For example, the immediate release component and/or the delayed release component may comprise PYR, PYL, PLP, PYM or PMP, or PYP, or any combination thereof (e.g., PYR+PYL, PYR+PLP, PYR+PYM, PYR+PMP, PYR+PYP, PYL+PLP, PYL+PYM, PYL+PMP, PLP+PYM, PLP+PMP, PYL+PYP, PYR+PYL+PLP, PYR+PYL+PYM, PYR+PYL+PMP, PYL+PLP+PYM, PYR+PYL+PYP, PYR+PLP+PMP, PYR+PLP+PYP, PYR+PYM+PMP, PLP+PYM+PYP, etc.).

In an embodiment, the above-mentioned immediate release component and/or delayed release component comprise a compound of formula I. In an embodiment, the immediate release component and the delayed release component comprise a compound of formula I. In another embodiment, only the immediate release component comprises a compound of formula I. In another embodiment, only the delayed release component comprises a compound of formula I.

In an embodiment, the immediate release component (A) comprises ingredients (a), (b) and (c), and the delayed release component (B) comprises ingredients (a), (b) and (c). In an embodiment, the immediate release component (A) comprises ingredients (a), (b) and (c), and the delayed release component (B) comprises ingredients (a) and (b). In an embodiment, the immediate release component (A) comprises ingredients (a), (b) and (c), and the delayed release component (B) comprises ingredients (b) and (c). In an embodiment, the immediate release component (A) comprises ingredients (a), (b) and (c), and the delayed release component (B) comprises ingredients (a) and (c). In an embodiment, the immediate release component (A) comprises ingredients (a), (b) and (c), and the delayed release component (B) comprises ingredient (a). In an embodiment, the immediate release component (A) comprises ingredients (a), (b) and (c), and the delayed release component (B) comprises ingredient (b). In an embodiment, the immediate release component (A) comprises ingredients (a), (b) and (c), and the delayed release component (B) comprises ingredient (c).

In an embodiment, the immediate release component (A) comprises ingredients (a) and (b), and the delayed release component (B) comprises ingredients (a), (b) and (c). In an embodiment, the immediate release component (A) comprises ingredients (a) and (b), and the delayed release component (B) comprises ingredients (b) and (c). In an embodiment, the immediate release component (A) comprises ingredients (a) and (b), and the delayed release component (B) comprises ingredients (a) and (c). In an embodiment, the immediate release component (A) comprises ingredients (a) and (b), and the delayed release component (B) comprises ingredient (c).

In an embodiment, the immediate release component (A) comprises ingredients (a) and (c), and the delayed release component (B) comprises ingredients (a), (b) and (c). In an embodiment, the immediate release component (A) comprises ingredients (a) and (c), and the delayed release component (B) comprises ingredients (b) and (c). In an embodiment, the immediate release component (A) comprises ingredients (a) and (c), and the delayed release component (B) comprises ingredients (a) and (b). In an embodiment, the immediate release component (A) comprises ingredients (a) and (c), and the delayed release component (B) comprises ingredient (b).

In an embodiment, the immediate release component (A) comprises ingredients (b) and (c), and the delayed release component (B) comprises ingredients (a), (b) and (c). In an embodiment, the immediate release component (A) comprises ingredients (b) and (c), and the delayed release component (B) comprises ingredients (a) and (c). In an embodiment, the immediate release component (A) comprises ingredients (b) and (c), and the delayed release component (B) comprises ingredients (a) and (b). In an embodiment, the immediate release component (A) comprises ingredients (b) and (c), and the delayed release component (B) comprises ingredient (a).

In an embodiment, the immediate release component (A) comprises ingredient (a), and the delayed release component (B) comprises ingredients (a), (b) and (c). In an embodiment, the immediate release component (A) comprises ingredient (a), and the delayed release component (B) comprises ingredients (b) and (c).

In an embodiment, the immediate release component (A) comprises ingredient (b), and the delayed release component (B) comprises ingredients (a), (b) and (c). In an embodiment, the immediate release component (A) comprises ingredient (b), and the delayed release component (B) comprises ingredients (a) and (c).

In an embodiment, the immediate release component (A) comprises ingredient (c), and the delayed release component (B) comprises ingredients (a), (b) and (c). In an embodiment, the immediate release component (A) comprises ingredient (c), and the delayed release component (B) comprises ingredients (a) and (b).

In an embodiment, the immediate release component (A) comprises ingredients (a) and (b) and the delayed release component (B) comprises ingredients (a), (b) and (c). In a further embodiment, the immediate release component (A) comprises Doxylamine or a salt thereof (e.g., Doxylamine succinate) and Pyridoxine or a salt thereof (e.g., Pyridoxine-HCl), and the delayed release component (B) comprises Doxylamine (e.g., Doxylamine succinate) or a salt thereof, Pyridoxine or a salt thereof (e.g., Pyridoxine-HCl) and a compound of formula I (e.g., a compound of formula I wherein R is OH, or a salt thereof).

In an embodiment, the dosage system comprises one or more dosage forms. In an embodiment, the dosage system comprises at least two dosage forms. In an embodiment, at least two of the dosage forms are the same, i.e. same ingredients, same doses, same excipients, same unit form (e.g., tablet). In another embodiment, all of the oral dosage forms are the same. In an embodiment, each of the different oral dosage forms comprises an identifying characteristic (e.g., shape, size, color, an identifying mark, any combination thereof) such that said different dosage forms can be distinguished from one another.

In another aspect, the present invention provides a dosage form comprising ingredients (a), (b) and (c) as defined above. In an embodiment, the dosage form is an oral dosage form. The terms "oral dosage form," "unit dose form", and the like are used interchangeably, and have their normal meaning in the art (i.e., refer to a pharmaceutical composition in the form of a tablet, capsule, caplet, gelcap, geltab, pill, flowable powder and the like).

In an embodiment, ingredients (a), (b) and (c) are in the same composition. In another embodiment, ingredients (a), (b) and (c) are in different compositions. For example, ingredients (a) and (b) may be in a first composition, and ingredient (c) in a second composition, or ingredients (a) may be in a first composition, and ingredients (b) and (c) in a second composition, etc.

Immediate Release

The term "immediate release component/composition" as used herein refers to a component/composition of a dosage form that is formulated to release substantially all the ingredient(s) (ingredients (a), (b) and/or (c)) within a relatively short period following administration with no enhanced, delayed or extended release effect. In some embodiments, the relatively short period can be, for example, within about 0.1 to about 2 hours, e.g., about 5, 10, 15, 20, 30, 40, 60, 90 or 120 minutes. In some embodiments, the immediate release component releases a majority of the ingredient(s), e.g., at least about 50%, 60%, 70%, 80%, 90%, 95% or 99% of active ingredient(s) from within the dosage form within such a relatively short period after administration. For example, about 80% of the ingredient can be released within about 15, 30 or 45 minutes after administration, as measured by standard dissolution assays such as those described herein. In an embodiment, the immediate release composition is for effecting release substantially (at least about 80 or 90% is released) within the stomach.

Delayed Release

The term "delayed release component/composition" as used herein refers to a component/composition of a dosage system/form that is formulated so as to have zero or relatively low release of the ingredient(s) during an initial period after administration to the subject, after which release occurs. The period is typically in the range of about 0.5 to 12, 18 or 24 hours, for example in the range of about 1 or 2 hours to about 6, 7, 8 or 9 hours, such as about 1, 2, 3, 4, 5, 6, 7, 8, or 9 hours. In embodiments, the delayed release begins after an initial period that is from about 2 hours to about 3 hours, or from about 3 hours to about 4 hours, or from about 4 hours to about 5 hours, or from about 5 hours to about 6 hours, after administration. In an embodiment, the delayed release composition is for effecting release substantially within the intestine, i.e., so that there is no or substantially no (less than about 10, 9, 8, 7, 6, 5, 4, 3, 2, or 1%) release in the stomach.

In an embodiment, although the delayed release component/composition from the dosage system/form commences to dissolve at a later time point than the immediate release component/composition, once release begins, the release pattern of the delayed release component/composition is similar to the pattern of the immediate release component/composition, described above. For example, a relatively short burst duration, for example less than 60 minutes, for instance less than about 50, 40, 30, 20, 15, 10, or 5 minutes, may be characteristic of both immediate release and delayed-burst release. Delayed-burst release can occur in a substantially unimpeded and/or relatively rapid manner once release begins. Many methods are known in the art for providing delayed-burst release, such as by diffusion, swelling, osmotic bursting or erosion (e.g., based on the inherent dissolution of the agent and incorporated excipients); certain methods are described below.

Coordination of Release

The immediate release and delayed release components/compositions result in two sequential releases of the ingredients, the first (immediate) release occurring relatively soon after administration and the second (delayed) release coming later. The time period between the first immediate release of the ingredients and the subsequent delayed release of the ingredients can be referred to as the "release interval." In unit dose forms of the invention, the release interval can generally be in the range of about 0.5 to 24, 18 or 12 hours, for example in the range of about 1 or 2 hours to about 6, 7, 8 or 9 hours, such as about 1, 2, 3, 4, 5, 6, 7, 8, or 9 hours. In embodiments, the delayed release begins after a period that is from about 2 hours to about 3 hours, or from about 3 hours to about 4 hours, or from about 4 hours to about 5 hours, or from about 5 hours to about 6 hours. Optionally, the delayed release is timed to occur at a time when the dosage form is found in the small intestine in fasting and/or fed subjects. The immediate release of ingredients can for example occur within about 1 hour after administration, for example within about 30 minutes or within about 15 minutes.

The release interval can be determined in vitro or in vivo. Although the plasma concentration of a drug can lag behind the actual time of release in the GI tract, the release interval can be approximately determined in vivo as the time interval between the $C_{max}$ (i.e., the maximum plasma concentration) of ingredient achieved by the immediate release component/composition and the $C_{max}$ of the ingredient achieved by the delayed release component/composition. Alternatively, the release interval can be monitored through the increased plasma concentration of the ingredient caused by delayed release following immediate release, compared to that achieved by only the immediate release of the ingredient.

Release can also be assessed using commonly used in vitro dissolution assays. Generally an in vitro dissolution assay is carried out by placing the dosage form(s) (e.g., tablet(s)) in a known volume of dissolution medium in a container with a suitable stirring device. An aliquot of the medium is withdrawn at various times and analyzed for dissolved active substance to determine the rate of dissolution. In one approach, the dosage form (e.g., tablet) is placed into a vessel of a United States Pharmacopeia dissolution apparatus II (Paddles) containing 900 or 1000 ml dissolution medium at 37° C. The paddle speed is 50, 75 or 100 RPM. Independent measurements are made for at least three (3) tablets, e.g., 6 tablets. The dissolution medium can be a neutral dissolution medium such as 50 mM potassium phosphate buffer, pH 7.2 ("neutral conditions") or water or an acidic medium such as 50 mM potassium (or sodium) acetate buffer, at pH 4.5. Typically a unit dose form is added to the vessel and dissolution is started. At specified times, e.g., 5, 10, 15, 20, 30, 45 or 60 minutes, an aliquot (e.g., 2 ml) of medium is withdrawn and the amount of active ingredient in solution is determined using routine analytical methods (e.g., HPLC).

By way of example, immediate release and/or delayed release of drug from the unit dosage form can be monitored using Apparatus II (Paddles) as described in U.S. Pharmacopeia, where the dissolution is conducted by placing one tablet into each of six vessels containing 1000 ml of release media with temperature at 37° C. and speed of 100 rpm. Optionally, the release media of 0.1N Hydrochloric acid (pH 1.2 or 4.5) is used for stage 1 for 2 hours, and 0.2M tribasic sodium phosphate buffer adjusted to pH 6.8 is used for stage 2 (Buffer stage) at 5, 10, 15, 20, 30, 45, 60, 90 and 120 minutes and assayed for drug content by HPLC. Further, various media for in vitro dissolution assays (e.g., simulated gastric fluid (SGF), simulated intestinal fluid (SIF), versions to simulate fed or fasting conditions (FeSSGF or FeSSIF for fed conditions, FaSSGF or FaSSIF for fasting conditions), etc.) may be used, which are well known in the art.

Methods and Agents to Effect Delayed Release

Delayed release can be effected by the use of one or more release-delaying agents. Any combination of release-delaying agents, including the ones described herein, can be used in the dosage forms. The release-delaying agent acts to increase the period before release begins from a dosage form. The length of the lag period before delayed release occurs can by controlled using methods known to those of skill in the art, for instance by varying the choice, combination, form, shape and/or amount of release-delaying agent(s).

The delayed release formulations can be prepared, for example, by coating ingredients or an ingredient-containing composition with one or more release-delaying agents. In other instances, the release-delaying agent(s) can be intermixed with or in co-solution with the ingredients. For example, delayed release by osmotic rupture can be achieved by a dosage form comprising one or more swelling agents that are contained in combination with the ingredients within a semipermeable coating. The increase in volume of the swelling agent upon exposure of the unit dosage form to bodily fluids causes the semipermeable coating to rupture. In such agents, both the swelling agent and the semipermeable coating can be considered to be release-delaying agents. Thus, delayed release can be achieved by a combination of release-delaying agents, where each release-delaying agent does not necessarily delay release by itself.

Delayed release can be achieved by various processes such as dissolution, diffusion, erosion (e.g., based on the inherent dissolution of the agent and incorporated excipients), and/or rupture (e.g., by swelling). Common mechanisms include bulk erosion of polymers which restrict diffusion of the drug, surface erosion, (e.g., of layered medicaments), or rupture. Rupture can be osmotically controlled, for instance by swelling which results from the osmotic infusion of moisture. Rupture can also result from the reaction of effervescent agents, e.g., citric acid/sodium bicarbonate, with water or other fluids that penetrate into the dosage form. Release, including delayed release, from a unit dosage form can be achieved by more than one mechanism. For example, release can occur for example by simultaneous swelling and diffusion, simultaneous diffusion and erosion, and simultaneous swelling, diffusion and erosion.

Methods of making delayed-burst release formulations are within ordinary skill. Examples are presented herein and can also be found in numerous publications, including U.S. Pat. Nos. 4,865,849, 4,871,549, 4,897,270, 5,017,381, 5,110,597, 5,260,068, 5,260,069, 5,387,421, 5,472,708, 5,508,040, 5,593,697, 5,840,329, 6,500,457, 6,531,152, 6,555,136, 6,627,223, 6,632,451 and 7,048,945.

Alternatively, delayed release can be initiated by a triggering signal such as a fluctuation in temperature, or an electromagnetic pulse. See, e.g., US Patent Publication Nos. 2001/6251365, 2006/997863, 2003/6514481, 2006/0057737, 2006/0178655, 2006/0121486, and 2006/0100608.

Two common classes of release-delaying agents are "enteric" (allowing release within a specific milieu of the gastro-intestinal tract) and "fixed-time" (allowing release after a "predetermined" or "fixed" time period after administration, regardless of gastro-intestinal milieu), each of which is discussed in more detail below. Enteric release-delaying agents for instance allow release at certain pHs or in the presence of degradative enzymes that are characteristically present in specific locations of the GI tract where release is desired. The dosage forms can comprise more than one release-delaying agent from any class, such as a combination of enteric and fixed-time release-delaying agents. In another embodiment, the release-delaying agent allows the release of drug after a predetermined period after the composition is brought into contact with body fluids ("fixed-time delayed release"). Unlike enteric release, fixed-time release is not particularly affected by environmental pH or enzymes.

A large number of fixed-time release-delaying agents are known to those of ordinary skill in the art. Exemplary materials which are useful for making the time-release coating of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose, cellulose acetate, cellulose acetate butyrate and ethyl cellulose; and other materials known to those of ordinary skill in the art. Other film-forming materials that can be used for this purpose include poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer. Other materials which can be used in the time-release coating include Acryl-EZE®, Eudragit® NE, RL and RS, Estacryl®, hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, and calcium pectinate can be included. Substances that are used as excipients within the pharmaceutical industry can also act as release-delaying agents.

Common types of fixed-time release dosage forms include erodible formulations, formulations that undergo osmotic rupture, or unit dosage form that use any combination of mechanisms for delayed release.

Fixed-time release-delaying agents can optionally achieve a delayed-burst release by osmotic rupture. Examples of such RDAs include swelling agents, osmogens, binders, lubricants, film formers, pore formers, coating polymers and/or plasticizers.

Osmotic rupture is achieved by a delayed release component which comprises a coated unit dosage form that contains the drug and a swelling agent within the semipermeable coating (e.g., ethylcellulose). The coating weight (thickness) of the semipermeable coating can be selected to delay release by osmotic rupture for a desired period. To identify the correct coating weight for a particular delay, unit dosage forms with a range of coating weights can be tested via in vitro dissolution to determine the burst time. Based on these results, a coating weight that achieves the desired lag period would be selected. In addition, the amount and/or ratio of a coating strength modifier (e.g., talc) in the coating can be adjusted as well. Other formulation variables that can also be adjusted to obtain the desired release by osmotic rupture include the amount of sweller layer and sweller and/or fillers in the formulation. In the case of rupturing tablets, the amount of sweller would be selected to achieve the target release, while still providing the tablet with sufficient compressibility and acceptably low friability to be manufacturable.

In an embodiment, the dosage form can comprise one or more "diffusion regulators" that control the permeation of bodily fluids into the drug-containing core. Exemplary diffusion regulators include hydrophilic polymers, electrolytes, proteins, peptides, amino acids and others known to those of ordinary skill in the pharmaceutical sciences. In an example, the fixed-time release-delaying agent comprises a coating that permits release of the ingredients after a fixed period. The thickness of the coating can affect the time required for penetration of fluids into the formulation. For example and without limitation, a diffusion controlling time release coating that provides release after a fixed delay period of about 0.5-2.5 hours could be about 200-1000 microns thick, and one that provides a release after a fixed delay period of about 2.5-5.0 hours could be about 1000-3000 microns thick.

Erodible formulations provide another example of fixed-time release formulations. The release delay from an erodible coated tablet can be adjusted by those of ordinary skill in the art by regulating the erodible layer coating weight. To identify the correct coating weight, tablets over a range of coating weights can be tested via in vitro dissolution (and/or erosion) to determine the burst time. Other formulation variables that may affect performance include the selection of the coating layer polymer type and viscosity. In an embodiment, the unit dosage form can comprise one or more "erosion regulators" that control the erosion rate of the coating. Any material or combination of materials may serve as an erosion regulator. Exemplary erosion and/or diffusion regulators include hydrophilic polymers, electrolytes, proteins, peptides, amino acids and others known to those of ordinary skill in the pharmaceutical sciences. The thickness of the coating can affect the time required for erosion of the coating. For example and not limitation, an erodible time-release coating that provides release after a fixed period of about 0.5-2.5 hours could be about 100-2000 microns thick, and one that provides release after a fixed delay period of about 2.5-5.0 hours could be about 2000-5000 microns thick.

The release-delaying agent may comprise an "enteric" material that is designed to allow release upon exposure to a characteristic aspect or environment of the gastrointestinal tract. In an embodiment, the enteric material is pH-sensitive and is affected by changes in pH encountered within the gastrointestinal tract (pH-sensitive release). The enteric material typically remains insoluble at gastric pH, then allows for release of the active ingredient in the higher pH environment of the downstream gastrointestinal tract (e.g., often the duodenum, or sometimes the colon). In another embodiment, the enteric material comprises enzymatically degradable polymers that are degraded by bacterial enzymes present in the lower gastrointestinal tract, particularly in the colon. Optionally, the unit dosage form is formulated with a pH-sensitive enteric material designed to result in a release within about 0-2 hours when at or above a specific pH. In various embodiments, the specific pH can for example be from about 4 to about 7, such as about 4.5, 5, 5.5, 6, 6.5 or 7.

Materials used for enteric release formulations, for example as coatings, are well known in the art and include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the trade-name Acryl-EZE® (Colorcon, USA), Eudragit® (Rohm Pharma; Westerstadt, Germany), including Eudragit® L30D-55 and L100-55 (soluble at pH 5.5 and above), Eudragit® L-IOO (soluble at pH 6.0 and above), Eudragit® S (soluble at pH 7.0 and above, as a result of a higher degree of esterification), and Eudragits® NE, RL and RS (water-insoluble polymers having different degrees of permeability and expandability), Estacryl®; vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different enteric materials may also be used. Multi-layer coatings using different polymers may also be applied. The properties, manufacture and design of enteric delivery systems are well known to those of ordinary skill in the art. See, e.g., Development of Biopharmaceutical Parenteral Dosage Forms (Drugs and the Pharmaceutical Sciences), by Bontempo (Publishers: Informa Healthcare (Jul. 25, 1997).

Those of ordinary skill in the art can adjust the period before delayed release from enteric coated multiparticulates by varying the enteric layer coating weight and composition. For example, where time in the stomach is <4 hours and some amount of protection (1-3 hours) is desired after the dosage form leaves the stomach, then an appropriate level of coating that provides up to 4 hours of protection between administration and drug release can be prepared.

Unit Dosage Forms

Monolithic dosage forms. In an embodiment, the unit dosage form is monolithic in nature, e.g., in the form of a tablet or capsule or a caplet (capsule-form tablet). Monolithic unit dosage forms may vary in shape and may be, for example, round, ovoid, oblong, cylindrical (e.g., disk shaped) or any other geometric shape, for example rectilinear. For example, the unit dosage form can have a disk or ovoid shape, or a shape like a flattened disk or torpedo. The edges can be beveled or rounded. The unit dosage form itself comprises two or three separate subunits, e.g., two compositions, one designed for immediate release of the active ingredients, and the second composition designed for delayed release of the ingredients. The unit dosage form can be provided in certain embodiments (e.g., non-monolithic embodiments) as a kit comprising separate components.

Multiparticulate forms. Although the unit dosage form may be a monolithic entity, the ingredients contained within the unit dosage form need not be in monolithic form. For instance, one or more ingredients can be multiparticulate in form. Ingredients in multiparticulate form for example comprise a plurality of drug-containing beads, particles or granules. Such multiparticulate forms are for instance incorporated into a unit dosage form that is a tablet or capsule.

Tablet/Capsule Combinations of Formulations—coated core tablets. One or more ingredients can be present in the form of a tablet or capsule within the unit dosage form. Ingredients in tablet form can be incorporated into a unit dosage form that is a capsule. Alternatively, tablet-type ingredients can be used as an inner core in a "coated core" tablet-type unit dosage form. In one such example, the unit dosage form comprises a multilayered tablet, with an inner core of ingredients for delayed release, and one or more outer layers that comprise ingredients for immediate release. In an embodiment, a unit dosage form comprising an enteric-coated tablet to provide the delayed release, contained within a larger tablet that contains the immediate release formulation.

Delayed release tablet or capsule in capsule dosage form. In another example, the delayed release component is in the form of a tablet or capsule, while the immediate release component is in the form of a flowable powder. The ingredients may be formulated independently or in combination. The final unit dosage form can be in the form of a capsule, and in such cases the delayed release component can be sized and shaped so as to be easily accommodated within the capsule, while allowing for inclusion of the immediate release component as well. As understood by those skilled in the art, the tablet or capsule configuration of the delayed release formulation may be specifically sized and shaped for such a purpose. Upon administration, the unit dosage form capsule releases the immediate release ingredients present in the flowable powder(s), and the delayed release tablet or capsule releases ingredients at a later time point.

In an embodiment, the unit dosage form can include more than one discrete and separable formulation, wherein each formulation comprises at least one ingredient of the unit dosage form. In such instances, the formulations can be separately prepared, and then combined into the final unit dosage form. In another embodiment, the ingredients can be co-formulated such that they are physically inseparable. In an embodiment, ingredients (a), (b) and (c) of the immediate release formulations are powders, and the unit dosage form comprises a powder blend in which particles containing ingredient (a) are intermixed with particles containing ingredient (b) and with particles containing ingredient (c). In another embodiment, a co-solution of ingredients (a), (b) and (c) is processed, e.g., by spray-drying or lyophilization, into an immediate release powder, wherein ingredients (a), (b) and (c) can be found together within a single particle of the powder. Optionally, ingredients (a), (b) and (c) can be in solid solution within such particles, and/or form a single continuous phase.

In an embodiment, the immediate release composition and the delayed release composition are comprised in the dual release dosage form in a layered arrangement with respect to one another. In another embodiment, the immediate release composition and the delayed release composition are comprised in the dual release dosage form adjacent to one another.

In an embodiment, the dual release oral dosage form comprises (i) a core comprising said delayed release composition and (ii) one or more coats substantially surrounding the core, said one or more coats comprising the immediate release composition. In an embodiment, the coating surrounding the core comprises an enteric coating, i.e. a coating made of enteric material as defined above. In a further embodiment, the dual release oral dosage form comprises (i) a core comprising said delayed release composition, the delayed release composition comprising ingredients (a), (b) and (c); (ii) an enteric coating surrounding said core, and (iii) a coating or shell surrounding said enteric coating and comprising the immediate release composition, the immediate release composition comprising ingredients (a) and (b).

In an embodiment, the dual release dosage form comprises (i) delayed release granules or microspheres comprising the delayed release composition and (ii) immediate release granules or microspheres comprising the immediate release composition.

In an embodiment, the immediate release composition is in contact with the delayed release composition, within said dual release dosage form. In another embodiment, the immediate release composition is not in contact with (i.e., spaced away from) the delayed release composition, within said dual release dosage form.

In an embodiment, the oral dosage form is adapted for once-a-day administration. In another embodiment, the oral dosage form is adapted for twice-a-day administration.

Manufacture of Dosage Forms

The ingredients may conveniently be presented in unit dosage form and may be prepared by any of the methods well known in the art of pharmacy. Techniques and formulations generally are found in for example Remington's Pharmaceutical Sciences (Mack Publishing Co., Easton, Pa.). Such methods include the step of bringing into association of one or more ingredients with any additional excipients. In general, the dosage forms are prepared by uniformly and intimately bringing into association the ingredients with liquid carriers or finely divided solid carriers or both, and then, if necessary, shaping the product or filling capsules.

In an embodiment, the unit dosage form and/or one or more formulations are in tablet form. Various methods of preparation of tablets are well known to one of ordinary skill in the art. See, e.g., Pharmaceutical Dosage Forms: Tablets, Third Edition, by Larry L. Augsburger and Stephen W. Hoag (Publisher: Informa Healthcare; Dec. 15, 2007). These methods include direct compression and granulation (e.g., wet or dry or fluid-bed).

The pellets can be made by, for example, simple granulation such as wet granulation or dry granulation, followed by sieving; extrusion and marumerization (spheronization); rotogranulation; or any agglomeration process that results in a pellet of reasonable size and robustness. For extrusion and marumerization, the ingredients and other additives are granulated by addition of a binder solution. The wet mass is passed through an extruder equipped with a certain size screen, and the extrudates are spheronized in a marumerizer. The resulting pellets are dried and sieved for further applications. One may also use high-shear granulation, wherein the drug and other additives are dry-mixed and then the mixture is wetted by addition of a binder solution in a high shear-granulator/mixer. The granules are kneaded after wetting by the combined actions of mixing and milling. The resulting granules or pellets are dried and sieved for further applications. Alternatively, the immediate release beadlets or pellets are prepared by solution or suspension layering, whereby a solution or dispersion of the ingredients, with or without a binder and optionally an anti-tacking agent such as talc, is sprayed onto a core or starting seed (either prepared or a commercially available product) in a fluid bed processor or other suitable equipment. The cores or starting seeds can be, for example, sugar spheres or spheres made from microcrystalline cellulose. The ingredients, thus, are coated on the surface of the starting seeds. The ingredients may also be layered onto the ingredients-containing pellets described above, if desired. Following drug layering, the resulting ingredients-loaded pellets are dried for further applications. A protective layer, or overcoating, may be desired to ensure that the ingredients-loaded pellets do not aggregate during processing or upon storage. The protective coating layer may be applied immediately outside the core, either an ingredients-containing core or an ingredients-layered core, by conventional coating techniques such as pan coating or fluid bed coating using solutions of polymers in water or suitable organic solvents or by using aqueous polymer dispersions. OPADRY®, OPADRY II® (Colorcon) and corresponding color and colorless grades from Colorcon can be used to protect the pellets from being tacky and provide colors to the product. Different anhydride-based polymers (e.g., sebacic/fumaric copolymers such as Spheromer™ I or Spheromer™ II from Spherics, Inc.) may also be used as protective layer. In certain embodiments, many ingredients can be incorporated into the overcoating formula, for example to provide a quicker immediate release, such as plasticizers: acetyltriethyl citrate, triethyl citrate, acetyltributyl citrate; dibutylsebacate, triacetin, polyethylene glycols, propylene glycol and the others; lubricants: talc, colloidal silica dioxide, magnesium stearate, calcium stearate, titanium dioxide, magnesium silicate, and the like.

In certain embodiments, the immediate release composition may be prepared as an uncoated tablet, or a tablet core prior to coating, comprising starch and a hydrophilic polymer acting as a matrix for a water-soluble drug or prodrug requires to have a certain minimum hardness in order to be able to resist breakage and/or attrition due to mechanical stresses imposed during a high-speed tableting operation (including all steps up to and including filling of the tablets into containers).

In yet other embodiments, the unit dosage form is in capsule form. Diverse capsule manufacturing and design methods are well known to one of ordinary skill in the art. See, e.g., Pharmaceutical Preformulation and Formulation: A Practical Guide from Candidate Drug Selection to Commercial Dosage Form, by Mark Gibson (publishers: Informa Healthcare, Aug. 1, 2001). When the unit dose form is a capsule, the method further comprises preparing the formulations into a form for loading and/or delivery, e.g., as a tablet, capsule and/or powder, and loading the formulations into the capsule to form the pharmaceutical unit dose.

Treatment or Alleviation of the Symptoms of Nausea and Vomiting

In another aspect, the present invention provides a method for alleviating the symptoms of nausea and vomiting, for example the symptoms of nausea and vomiting of human pregnancy (NVP), said method comprising administering to a human subject in need thereof the dosage system or dosage form defined above.

In another aspect, the present invention provides a method for alleviating the symptoms of nausea and vomiting, for example the symptoms of nausea and vomiting of human pregnancy (NVP), said method comprising administering to a human subject in need thereof:
(a) one or more of (i) Doxylamine, (ii) an analog thereof, (iii) a derivative thereof, (iv) a prodrug thereof, (v) a metabolite thereof and (vi) a salt of any of (i)-(v);
(b) one or more of (i) Pyridoxine, (ii) an analog thereof, (iii) a derivative thereof, (iv) a prodrug thereof, (v) a metabolite thereof and (vi) a salt of any of (i)-(v); and
(c) one or more compounds of formula (I)

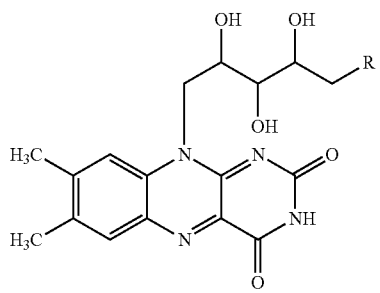

wherein R is a hydroxyl group, a phosphate group or

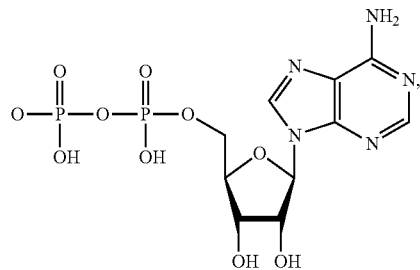

or a pharmaceutically acceptable salt thereof.

In another aspect, the present invention provides the use of:
(a) one or more of (i) Doxylamine, (ii) an analog thereof, (iii) a derivative thereof, (iv) a prodrug thereof, (v) a metabolite thereof and (vi) a salt of any of (i)-(v);
(b) one or more of (i) Pyridoxine, (ii) an analog thereof, (iii) a derivative thereof, (iv) a prodrug thereof, (v) a metabolite thereof and (vi) a salt of any of (i)-(v); and
(c) one or more compounds of formula (I)

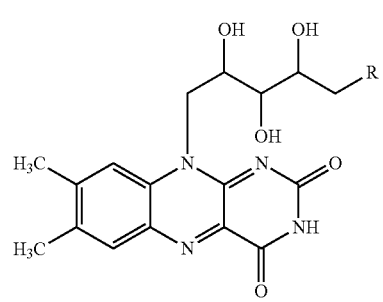

wherein R is a hydroxyl group, a phosphate group or

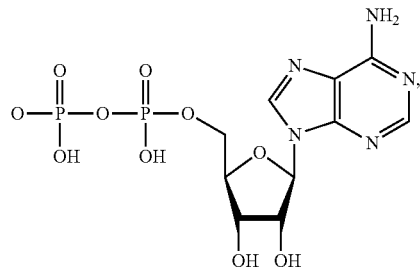

or a pharmaceutically acceptable salt thereof, for alleviating the symptoms of nausea and vomiting, for example the symptoms of nausea and vomiting of human pregnancy (NVP).

In another aspect, the present invention provides the use of:
(a) one or more of (i) Doxylamine, (ii) an analog thereof, (iii) a derivative thereof, (iv) a prodrug thereof, (v) a metabolite thereof and (vi) a salt of any of (i)-(v);
(b) one or more of (i) Pyridoxine, (ii) an analog thereof, (iii) a derivative thereof, (iv) a prodrug thereof, (v) a metabolite thereof and (vi) a salt of any of (i)-(v); and (c) one or more compounds of formula (I)

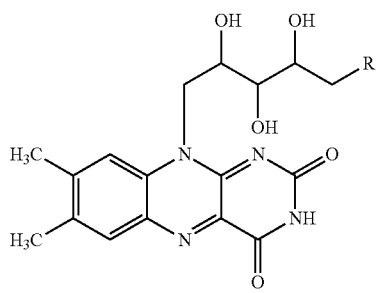

wherein R is a hydroxyl group, a phosphate group or

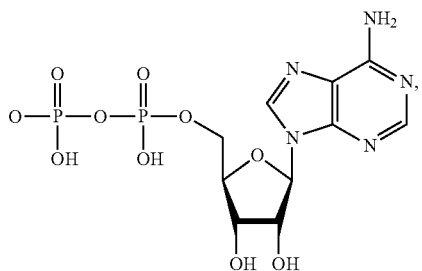

or a pharmaceutically acceptable salt thereof, for the preparation of a medicament for alleviating the symptoms of nausea and vomiting, for example the symptoms of nausea and vomiting of human pregnancy (NVP).

In another aspect, the present invention provides a method for alleviating the symptoms of nausea and vomiting in a human subject, said method comprising administering an effective amount of the above-mentioned dosage system or dosage form to a human subject in need thereof.

In another aspect, the present invention provides a method for alleviating the symptoms of nausea and vomiting of human pregnancy (NVP), the method comprising administering an effective amount of the above-mentioned dosage system or oral dosage form to a pregnant human female in need thereof.

In another aspect, the present invention provides a use of the above-mentioned dosage system or dosage form for alleviating the symptoms of nausea and vomiting in a human subject.

In another aspect, the present invention provides a use of the above-mentioned dosage system dosage form for alleviating the symptoms of NVP.

In another aspect, the present invention provides a use of the above-mentioned dosage system or dosage form for the preparation of a medicament for alleviating the symptoms of nausea and vomiting in a human subject.

In another aspect, the present invention provides a use of the above-mentioned dosage system or dosage form for the preparation of a medicament for alleviating the symptoms of NVP.

In another aspect, the present invention provides the above-mentioned dosage system or dosage form for use in alleviating the symptoms of nausea and vomiting in a human subject.

In another aspect, the present invention provides the above-mentioned dosage system or dosage form for use in the preparation of a medicament for alleviating the symptoms of NVP.

In another aspect, the present invention provides the above-mentioned dosage system or dosage form for use in the preparation of a medicament for alleviating the symptoms of nausea and vomiting in a human subject.

In another aspect, the present invention provides the above-mentioned dosage system or dosage form for use in alleviating the symptoms of NVP.

In an embodiment, the amount/dosage of ingredients (a), (b) and (c) are as defined above.

In an embodiment, the above-mentioned at least two dosage forms are for administration from two to four times a day (i.e., within a 24 h period). In an embodiment, the administration is according to the following schedule: a first dosage form in the evening (e.g., at about 10 PM), a second dosage form in the morning (e.g., at about 8 AM) and a third dosage form in the afternoon (e.g., at about 4 PM). In embodiments, the first, second and/or third dosage forms may be identical or different. In an embodiment, the first, second and/or third dosage forms are identical.

In another embodiment, the administration is according to the following schedule: a first dosage form in the evening (e.g., at about 10 PM) and a second dosage form in the morning (e.g., at about 10 AM). The first and second dosage forms may be the same or different. In an embodiment, the first and second dosage forms are identical.

In an embodiment, the above-mentioned at least two dosage forms are for administration under fed (e.g., during a meal or less than 2 hrs before or after meal) and/or fasted conditions (e.g., at least 2 hrs before or after meal).

In another embodiment, the above-mentioned method or use comprises a once-daily administration (a single dosage form is administered each day). In another embodiment, the above-mentioned method or use comprises a twice-daily administration (two dosage forms are administered each day).

In another aspect, the present invention provides a kit for alleviating the symptoms of nausea and vomiting in a human subject, the kit comprising the above-mentioned dosage system or dosage form. In an embodiment, the kit further comprises instructions for using the dosage system or dosage form for alleviating the symptoms of nausea and vomiting in a human subject. The kit may further comprise one or more containers.

In another aspect, the present invention provides a kit for alleviating the symptoms of nausea and vomiting of human pregnancy (NVP), the kit comprising the above-mentioned oral dosage system or dosage form. In an embodiment, the kit further comprises instructions for using the dosage system or dosage form for alleviating the symptoms of NVP. The kit may further comprise one or more containers.

In an embodiment, the kit comprises at least two dosage forms identified to be taken at different times of the day. For example, the kit may comprise a first dosage form comprising an indicator (shape, color, markings, etc.) that it has to be taken at a certain time of the day (e.g., in the evening, e.g., at about 10 PM), and a second dosage form comprising an indication (shape, color, markings, etc.) that it has to be taken at another time of the day (e.g., in the morning, e.g., at about 10 AM). At least two dosage forms may be identical or different.

In another embodiment, the kit comprises instructions for using the dosage system dosage form according to the following schedule: a first dosage form in the evening (e.g., at about 10 PM) and a second dosage form in the morning (e.g., at about 10 AM). The first and second dosage forms may be the same or different. In an embodiment, the first and second dosage forms are identical.

In an embodiment, the kit further comprises a container in which the above-mentioned dosage system or dosage form is packaged.

The kit according to the invention is preferably designed for in each case twice daily administration of the dosage forms contained therein. The kit preferably comprises all the dosage forms which are necessary for administration for a certain period of time (1 week, 2 weeks, 3 weeks, 1 month), for example according to a particular treatment regimen. The kit may also contain instructional materials, markings or arrangements which explain the use and order of the dosage forms. The dosage forms may be packaged to visually and/or tactilely indicate an appropriate time and/or sequence for administering the dosage forms in the kit.

In an embodiment, the kit comprises a pharmaceutical dosage form bearing a pregnancy-friendly indicium to graphically confirm the non-teratogenic aspect of said dosage form. Examples of such pregnancy-friendly indicia are described in PCT publication No. WO/2004/004694. In an embodiment, the indicium is the shape of a graphical illustration of a pregnant woman applied to the dosage form itself or to the container/package.

In another aspect, the present invention provides a method for improving the pharmacokinetics of PLP (e.g., decreasing the time of appearance or accelerating the appearance, decreasing the time to reach the steady state level) of PLP in the plasma in a subject administered with Pyridoxine or a salt thereof, said method comprising administering to said subject one or more compounds of formula I or a salt thereof as defined above.

In another aspect, the present invention provides a method for improving the bioavailability of PLP in the plasma in a subject administered with Pyridoxine or a salt thereof, said method comprising administering to said subject one or more compounds of formula I or a salt thereof as defined above.

In another aspect, the present invention provides a method for improving the rate of action of Pyridoxine or a salt thereof in a subject, said method comprising administering to said subject one or more compounds of formula I or a salt thereof as defined above.

In another aspect, the present invention provides a method for improving the prevention and/or treatment of NVP in a subject administered with Pyridoxine or a salt thereof, said method comprising administering to said subject one or more compounds of formula I or a salt thereof as defined above.

In another aspect, the present invention provides the use of one or more compounds of formula I or a salt thereof as defined above for improving the rate of action of Pyridoxine or a salt thereof in a subject.

In another aspect, the present invention provides the use of one or more compounds of formula I or a salt thereof as defined above for improving the pharmacokinetics of PLP (e.g., decreasing the time of appearance or accelerating the appearance, decreasing the time to reach the steady state level) of PLP in the plasma in a subject using Pyridoxine or a salt thereof.

In another aspect, the present invention provides the use of one or more compounds of formula I or a salt thereof as defined above for improving the bioavailability of PLP in the plasma in a subject using Pyridoxine or a salt thereof.

In another aspect, the present invention provides the use of one or more compounds of formula I or a salt thereof as defined above for improving the prevention and/or treatment of NVP in a subject using Pyridoxine or a salt thereof.

In an embodiment, the one or more compounds of formula I or salt thereof is/are administered or used before the administration or use of the Pyridoxine or salt thereof. In another embodiment, the one or more compounds of formula I or salt thereof is/are administered or used concurrently with the administration or use of the Pyridoxine or salt thereof.

In an embodiment, the "subject" or "patient" is a human subject. In a further embodiment, the subject is a human female, in a further embodiment the subject is a pregnant human female.

MODE(S) FOR CARRYING OUT THE INVENTION

The present invention is illustrated in further details by the following non-limiting examples.

Example 1

Management of Nausea and Vomiting of Pregnancy Symptoms—Correlation with Doxylamine and PLP Levels A randomized controlled efficacy trial of Diclectin® vs. placebo in pregnant women was carried out as follows, with the results shown in FIG. 1.

Objective:

To assess the plasma levels of Doxylamine and PLP and the severity of nausea and vomiting of pregnancy symptoms in pregnant women treated with Diclectin®.

Subjects

The demographic and medical characteristics of the subjects are as described in Koren et al., *Am J Obstet Gynecol* 2010; 203(6):571.e1-7.

Study Design:

The study design is as described in Koren et al., 2010, supra. Briefly, a randomized, double-blind, multicenter placebo controlled trial studying pregnant women suffering from nausea and vomiting of pregnancy, analyzed by intention to treat. Women received Diclectin (n=131) or placebo (n=125) for 14 days. Nausea and vomiting of pregnancy symptoms were evaluated daily using the pregnancy unique quantification of emesis scale (PUQE-24, Ebrahimi et al., *J Obstet Gynaecol Can.* 2009 September; 31(9):803-7). Doxylamine, and Pyridoxine and its metabolites were measured using liquid chromatography-tandem mass spectrometry, as previously described (Nulman and Koren, *Can J Clin Pharmacol* Vol 16 (3):e400-e406, 2009).

Figure 1:
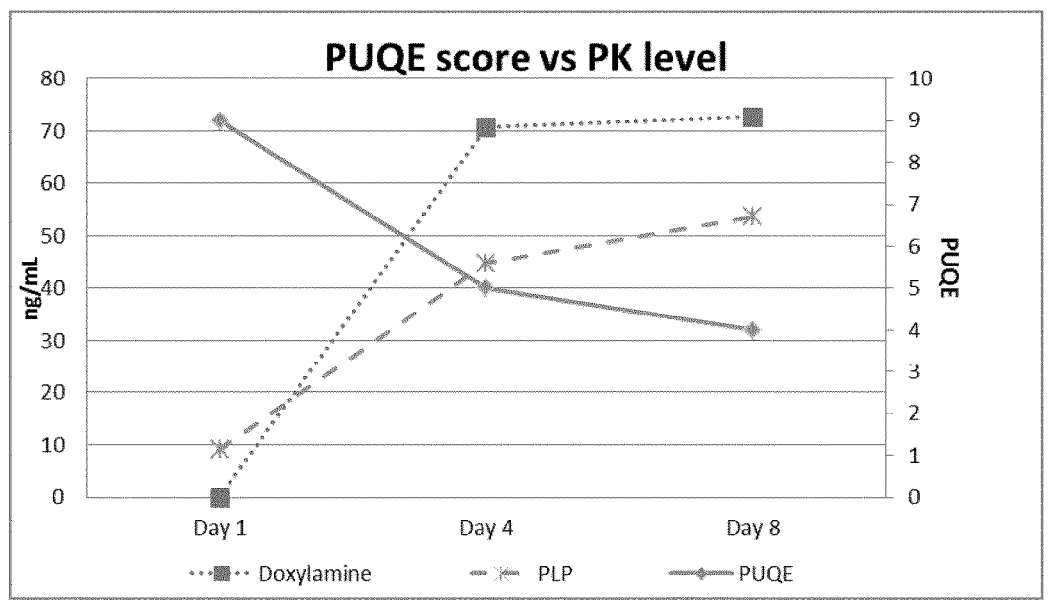
FIG. 1 shows the average plasma levels (left axis) of Doxylamine and PLP (Pyridoxal 5-phosphate, a Pyridoxine metabolite) in subjects at the indicated time points following administration of Diclectin®, vs. the results of the Pregnancy-Unique Quantification of Emesis and nausea (PUQE) score, which is representative of the severity of the NVP.

Results:

The results shown in FIG. 1 indicate that the increase in average plasma concentration of Doxylamine and PLP correlates with a decrease in the severity of the NVP (as assessed by the PUQE score), thus indicating that an increase of plasma concentration of Doxylamine and PLP correlates with a reduction in the severity of NVP, and therefore increasing the plasma levels of these compounds may be used for the treatment of NVP. Notably, these results indicate that among the various metabolites of Pyridoxine, PLP appears to be a metabolite which is effective in reducing the severity of NVP.

Example 2

Effect of Pyridoxine Metabolites and Riboflavin-5-phosphate on the Pharmacokinetics of Doxylamine, Pyridoxine and Pyridoxine Metabolites—Study Design and Results The results depicted in FIGS. 2 and 3 were obtained from randomized controlled bioavailability studies in healthy women, which were carried out as follows.

Objective:

To characterize the pharmacokinetic profile of Pyridoxal-5'-Phosphate (PLP) and to determine whether Riboflavin-5-phosphate (R5P), PLP or PYL in an immediate release formulation can be used to positively alter the kinetics of PLP compared to the current Diclectin® formulation (the current Diclectin® formulation is a delayed release formulation containing 10 mg Doxylamine succinate and 10 mg Pyridoxine-HCl).

Subjects:

Healthy female (n=12) participants between 18 and 45 years of age with a body mass index between 19 and 30 kg/m$^2$ were administered the treatments described below under empty stomach (fasted) conditions. Blood sampling was conducted extensively from 1 hour pre-administration until 24 hours post-administration. After a wash-out period of 21 days, dose administration and blood sampling was re-conducted as stated above. Doxylamine, Pyridoxine and Pyridoxine metabolites were measured using liquid chromatography-tandem mass spectrometry, as previously described (Nulman and Koren, Can J Clin Pharmacol Vol 16(3):e400-e406, 2009).

Study Design:

Three Way Cross Over Design.

Formulations:

Diclectin®: delayed release formulation containing 10 mg Doxylamine succinate and 10 mg Pyridoxine-HCl (PA-DR).

Immediate release: an oral solution of 20 mg Doxylamine succinate and 20 mg Pyridoxine-HCl (PA-IR).

Treatment group A: One (1) Diclectin® Tablet (current delayed release formulation of 10 mg Doxylamine and 10 mg Pyridoxine-HCl) plus an oral solution of 10 mg Doxylamine and 10 mg Pyridoxal HCl (immediate release) (PYL);

Treatment group B: One (1) Diclectin® Tablet (current delayed release formulation of 10 mg Doxylamine and 10 mg Pyridoxine-HCl) plus an oral solution of 10 mg Doxylamine and 10 mg Pyridoxal-5'-Phosphate (immediate release) (PLP);

Treatment group C: One (1) Diclectin® Tablet (current delayed release formulation of 10 mg Doxylamine and 10 mg Pyridoxine-HCl) plus an oral solution of 10 mg Doxylamine and 10 mg Pyridoxine HCl and 40 mg Riboflavin-5-phosphate (R5P) (immediate release).

Parameters Analyzed:

Bioavailability; $T_{max}$, $C_{max}$ and $AUC_{0-t}$ between each treatment. Doxylamine, and Pyridoxine and its metabolites were measured using liquid chromatography-tandem mass spectrometry, as previously described (Nulman and Koren, *Can J Clin Pharmacol* Vol 16 (3):e400-e406, 2009).

Figure 2:
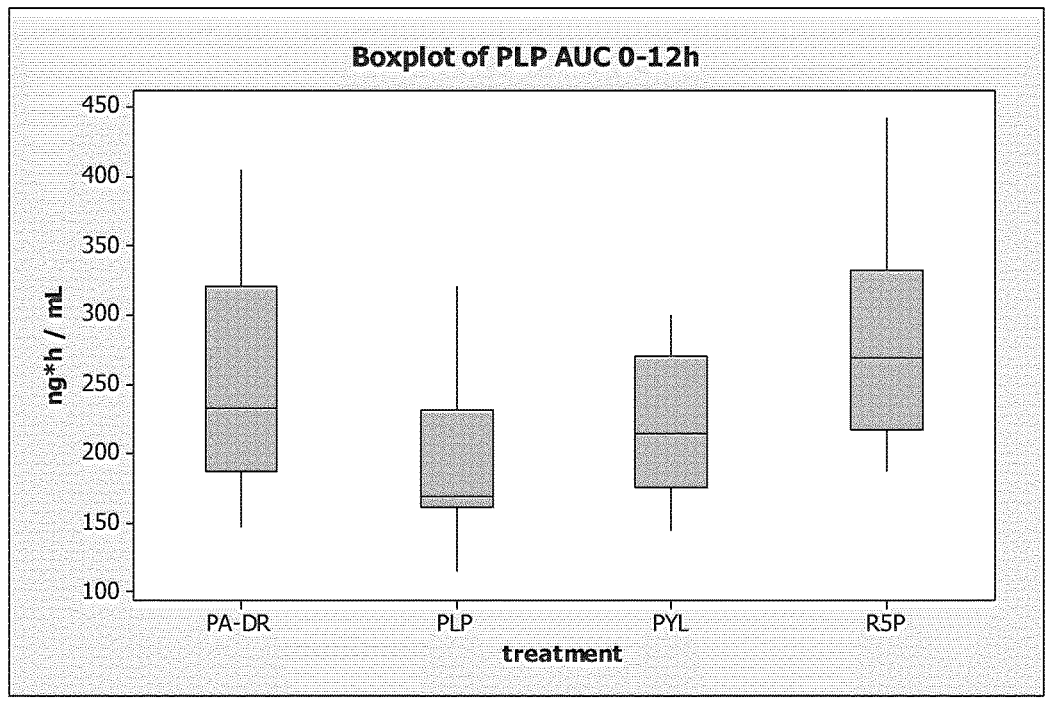
FIG. 2 shows a boxplot of the PLP concentration (as measured by the area under the curve, AUC) for the period of 0-12 h after dosing and the results of One-way ANOVA analysis for the different groups of subjects; PA-DR=two Diclectin® tablets, delayed released formulation comprising 10 mg Doxylamine succinate and 10 mg Pyridoxine-HCl per tablet; PLP=One Diclectin® tablet plus an oral solution of 10 mg Doxylamine succinate and 10 mg Pyridoxal-5'-Phosphate; PYL=One Diclectin® tablet plus an oral solution of 10 mg Doxylamine succinate and 10 mg Pyridoxal-HCl; R5P=One Diclectin® tablet plus an oral solution of 10 mg Doxylamine succinate, 10 mg Pyridoxine-HCl and 40 mg riboflavin-5-phosphate (I)

Results:

The results depicted in FIG. 2 show that when comparing the PLP concentration (using AUC) over the period 0-12 h, there is no significant difference (one-way ANOVA P>0.05) between Diclectin® (PA_DR) and any of the 3 treatments (A, B and C) described above. Results of PLP AUC from 0-12 h that shows that over a 12 h-period, R5P did not increase PLP levels significantly, and the other treatments resulted in lower PLP levels.

Figure 3:
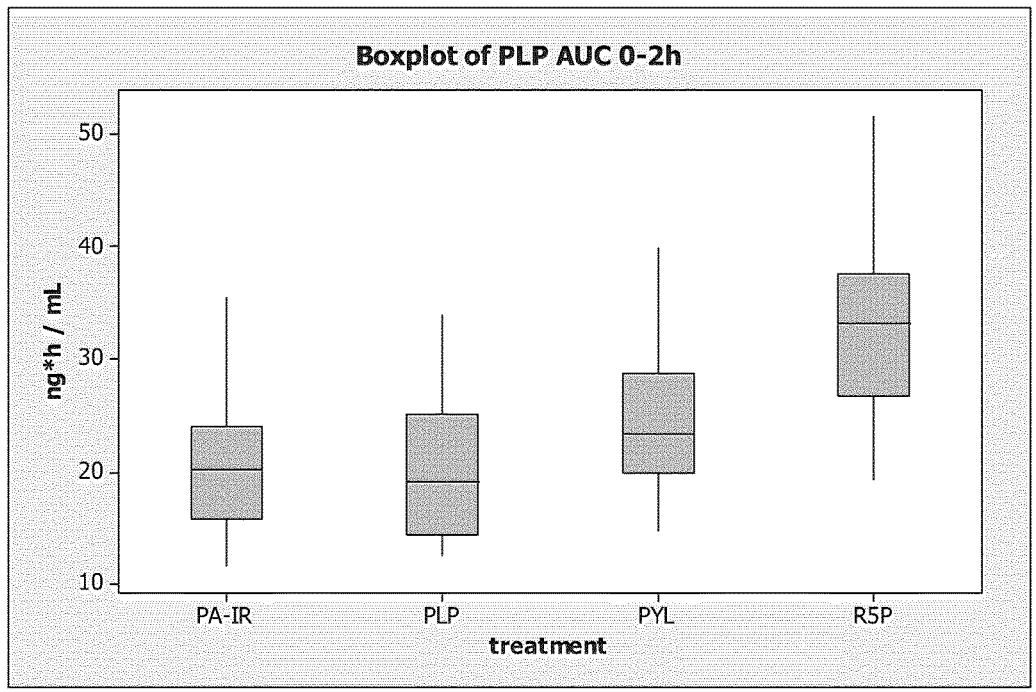
FIG. 3 shows a boxplot of the PLP concentration (as measured by the area under the curve, AUC) for the period of 0-2 h after dosing and the results of One-way ANOVA analysis for the different groups of subjects; PA-IR=a solution of 20 mg Doxylamine succinate and 20 mg of Pyridoxine-HCl equivalent to two Diclectin® tablets but in immediate release format; PLP=One Diclectin® tablet plus an oral solution of 10 mg Doxylamine succinate and 10 mg Pyridoxal-5'-Phosphate; PYL=One Diclectin® tablet plus an oral solution of 10 mg Doxylamine succinate and 10 mg Pyridoxal-HCl; R5P=One Diclectin® tablet plus an oral solution of 10 mg Doxylamine succinate, 10 mg Pyridoxine-HCl and 40 mg riboflavin-5-phosphate (I)

FIG. 3 shows that over the period of 0-2 h, there is a significant difference (p<0.05) when comparing the treatments A (PYL) and C (R5P) with a formulation equivalent to an immediate release formulation of Doxylamine succinate and Pyridoxine-HCl (PA-IR). The boxplot shows that treatments A (PYL) and C (R5P) result in an increase level of PLP over the period of 0-2 h when compared to the immediate release (PA-IR), but that the increase is more pronounced with R5P (treatment C), with PLP levels about 50% higher relative to that measured with the IR formulation. However, direct administration of PLP via the addition of PLP in the immediate release formulation (treatment B, PLP) resulted in plasma PLP levels similar to those obtained following administration of an immediate release formulation of Doxylamine succinate and Pyridoxine-HCl (PA-IR) over the period of 0-2 h. The results depicted in FIGS. 2 and 3 thus demonstrate that while it does not significantly affect PLP levels at 12 h, co-administration of 40 mg of R5P leads to a faster increase in the plasma level of PLP (AUC 0-2 h) following administration of Pyridoxine. Further, co-administration of R5P resulted in a faster increase in plasmatic PLP levels which was not obtained by direct administration of PLP itself. As such, these results demonstrate that plasma levels of the active metabolite PLP may be increased more quickly via the administration of R5P. Also, these results provide evidence that administration of R5P is associated with general improvement in the pharmacokinetic profile, including less inter-subject variations and decreased time to reach steady-state PLP levels. In another study, different doses of R5P were tested: 5, 10 or 20 mg of R5P (i.e. equivalent to the formulations administered to Treatment group C above, with the exception that 5, 10 or 20 mg of R5P was used rather than 40 mg R5P; 8 healthy women for each dose), and the PLP levels were compared to those measured in control healthy women not administered with R5P (24 subjects, equivalent to Treatment group A above). The pharmacokinetic results showed that the administration of 5 or 10 mg of R5P had no significant effect on PLP levels (i.e. not significantly different than controls), whereas the administration of 20 mg of R5P led to some improvement in the pharmacokinetics of PLP (e.g., a faster increase in the plasma level of PLP) relative to controls. The effect observed with administration of 20 mg of R5P was lower than that observed in subjects administered with 40 mg of R5P.

Example 3

Figure 4:
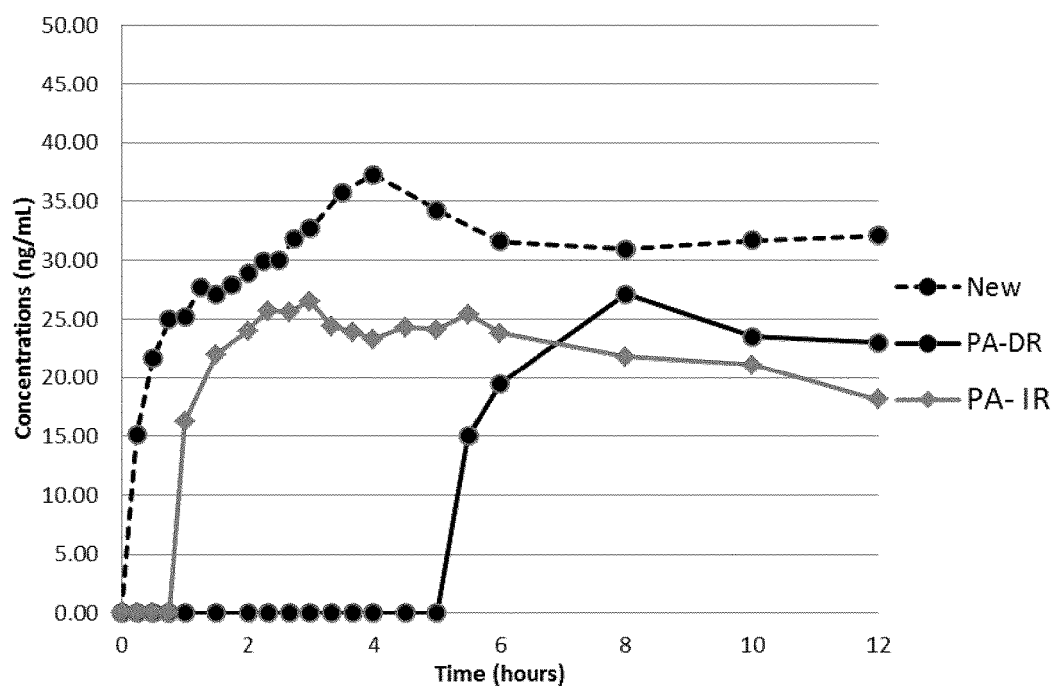
FIG. 4 shows a comparison of the plasma concentrations of PLP in (1) healthy women who took two Diclectin® tablets (PA-DR; 20 mg Doxylamine succinate and 20 mg Pyridoxine-HCl in delayed release format), (2) healthy women who took the equivalent dose in immediate release format (PA-IR; oral solution of 20 mg Doxylamine succinate and 20 mg Pyridoxine-HCl), and (3) healthy women who took one Diclectin® tablet (10 mg Doxylamine succinate and 10 mg Pyridoxine-HCl in delayed release format) plus an oral solution (immediate release) of 10 mg Doxylamine succinate, 10 mg Pyridoxine-HCl and 40 mg riboflavin-5-phosphate (New)

Comparative Bioavailability of Diclectin Delayed Release Vs an Equivalent Dose in Oral Solution (Immediate Release)—Study Design and Results The results depicted in FIG. 4 were obtained from randomized controlled bioavailability studies in healthy women.

Objective:

To characterize the bioavailability of Doxylamine, Pyridoxine and its metabolites after the administration of Diclectin delayed release and an equivalent dose in immediate release.

Subjects:

Healthy female (n=18) participants between 18 and 45 years of age with a body mass index between 19 and 30 kg/m$^2$ were administered the treatments described below under empty stomach (fasted) conditions. Blood sampling was conducted extensively from 1 hour pre-administration until 24 hours post-administration. After a wash-out period of 21 days, dose administration and blood sampling was re-conducted as stated above. Doxylamine, Pyridoxine and Pyridoxine metabolites were measured using liquid chromatography-tandem mass spectrometry, as previously described (Nulman and Koren, *Can J Clin Pharmacol Vol* 16 (3):e400-e406, 2009).

Study Design:
Two-Way Cross Over Design.
Formulations:
Treatment group A (PA-DR): Two (2) Diclectin® Tablets (current delayed release formulation)
Treatment group B (PA-IR): An oral solution of 20 mg Doxylamine succinate and 20 mg Pyridoxine-HCl (immediate release).
Parameters Analyzed:
Bioavailability; $T_{max}$, $C_{max}$ and $AUC_{0-t}$ between each treatment.

The results were compared to those obtained with treatment group C of Example 2 above, and are depicted in FIG. 4. FIG. 4 shows the pharmacokinetic profile of Doxylamine and PLP following administration of (1) two Diclectin® tablets (PA-DR), (2) an equivalent dose in immediate release format (PA-IR), and (3) one Diclectin® tablet (10 mg Doxylamine succinate and 10 mg Pyridoxine-HCl in delayed release format) plus an oral solution (immediate release) of 10 mg Doxylamine succinate, 10 mg Pyridoxine-HCl and 40 mg riboflavin-5-phosphate (New), in healthy women. These results show the improved bioavailability (e.g., faster appearance of PLP in the plasma) following administration of a combined delayed release (Diclectin®) tablet and an oral solution (immediate release) comprising Doxylamine succinate, Pyridoxine-HCl and riboflavin-5-phosphate, relative to the administration of Diclectin® only, or to an equivalent administration of Diclectin® in an immediate release format.

From the above it will be appreciated that in a dosage regimen involving the administration of Pyridoxine (or an analog, derivative, prodrug, metabolite and/or a salt thereof), the pharmacokinetic profile of PLP (e.g., faster appearance of PLP in the plasma, less inter-subject variations in PLP levels, and/or decreased time to reach steady-state PLP levels) may be improved through administration of R5P (or its precursor riboflavin or the metabolite FAD).

Although the present invention has been described hereinabove by way of specific embodiments thereof, it can be modified, without departing from the spirit and nature of the subject invention as defined in the appended claims. The scope of the claims should not be limited by the preferred embodiments set forth in the examples, but should be given the broadest interpretation consistent with the description as a whole. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A method for improving the bioavailability of pyridoxal 5-phosphate (PLP) in the plasma in a subject in need of treatment with PLP, said method comprising administering to the subject, as active ingredients, the following ingredients: (i) about 30 mg to about 100 mg of a riboflavin compound selected from (a) riboflavin or a pharmaceutically acceptable salt thereof, (b) riboflavin-5-phosphate or a pharmaceutically acceptable salt thereof, and (c) flavin adenine dinucleotide or a pharmaceutically acceptable salt thereof, (ii) pyridoxine or a pharmaceutically acceptable salt thereof, and optionally (iii) doxylamine or a pharmaceutically acceptable salt thereof, thereby administration of said riboflavin compound improves the bioavailability of PLP in the plasma in said subject, wherein the improved bioavailability of PLP is measurable by the increased PLP in the area under the curve for a period of 0 to 2 hours.

2. The method of claim 1, wherein the riboflavin compound is riboflavin.

3. The method of claim 1, wherein the riboflavin compound is riboflavin-5-phosphate.

4. The method of claim 1, wherein the method comprises administering to the subject about 30 mg to about 50 mg of the riboflavin compound.

5. The method of claim 1, wherein the subject is administered about 5 mg to about 40 mg of the pyridoxine or the pharmaceutically acceptable salt thereof.

6. The method of claim 5, wherein the subject is administered about 10 mg to about 30 mg of the pyridoxine or the pharmaceutically acceptable salt thereof.

7. The method of claim 1, wherein the pyridoxine or the pharmaceutically acceptable salt thereof is pyridoxine hydrochloride.

8. The method of claim 1, wherein the active ingredients are in the same pharmaceutical composition.

9. The method of claim 8, wherein the pharmaceutical composition comprises doxylamine or a pharmaceutically acceptable salt thereof.

10. The method of claim 9, wherein the doxylamine or the pharmaceutically acceptable salt thereof is doxylamine succinate.

11. The method of claim 10, wherein the doxylamine or the pharmaceutically acceptable salt thereof is present in an amount of about 5 mg to about 40 mg in said pharmaceutical composition.

12. The method of claim 11, wherein the doxylamine or the pharmaceutically acceptable salt thereof is present in an amount of about 10 mg to about 30 mg in the pharmaceutical composition.

13. The method of claim 8, wherein the pharmaceutical composition is an oral dosage form.

14. The method of claim 13, wherein the oral dosage form is a tablet or a pill.

15. The method of claim 13, wherein the oral dosage form comprises an immediate release component and a delayed release component.

16. The method of claim 8, wherein said subject is a pregnant female subject.

17. The method of claim 16, wherein said pregnant female subject has symptoms of nausea and vomiting of human pregnancy (NVP).

18. The method of claim 8, wherein the pharmaceutical composition comprises about 10 mg to about 30 mg of pyridoxine hydrochloride and about 30 mg to about 50 mg of riboflavin.

19. The method of claim 18, wherein the pharmaceutical composition comprises about 10 mg to about 30 mg of doxylamine succinate.

* * * * *